United States Patent [19]

Birmingham et al.

[11] Patent Number: 4,889,809
[45] Date of Patent: Dec. 26, 1989

[54] **TYLOSIN RESISTANCE-CONFERRING GENE, DESIGNATED TLRC, FOR USE IN *STREPTOMYCES FRADIAE***

[75] Inventors: Virginia A. Birmingham, Carmel; Karen L. Cox, Martinsville; Eugene T. Seno, Indianapolis, all of Ind.

[73] Assignee: Eli Lilly and Company, Indianapolis, Ind.

[21] Appl. No.: 890,993

[22] Filed: Jul. 25, 1986

[51] Int. Cl.⁴ .................. C12N 1/20; C12N 15/00; C12N 7/00; C12P 21/00; C12P 19/34; C12R 1/54; C07H 15/12

[52] U.S. Cl. .................. 435/252.3; 435/69.1; 435/91; 435/172.1; 435/172.3; 435/253.5; 435/320; 435/896; 536/27; 935/19; 935/29; 935/41; 935/56; 935/60; 935/75; 935/81

[58] Field of Search ............ 435/68, 91, 172.3, 253, 435/320, 186, 896; 535/27; 935/19, 29, 41, 56, 60, 75, 81

[56] References Cited

U.S. PATENT DOCUMENTS 653,975 9/1984 Seno et al. .
871,051 6/1886 Seno et al. .

OTHER PUBLICATIONS

Benveniste and Davies, 1973, Proc. Natl. Acad. Sci. USA 70(8): 2276-2280.
Thompson et al., 1980, Nature 286:525-527.
Fujisawa and Weisblum, 1981, J. Bacteriol. 146(2):621-631.
Thompson et al., 1982, J. Bacteriol. 151(2):668-677.
Thompson et al., 1982, J. Bacteriol. 151(2):678-685.
Thompson et al., 1982, Gene 20:51-62.
Murakami et al., 1983, J. Antibiotics 36(10):1305-1311.
Tohyama et al., 1984, J. Antibiotics 37(12):1736-1737.
Nakano et al., 1984, J. Bacteriol. 157(1):79-83.
Bibb. et al., 1985, Mol. Gen. Genet. 199:26-36.
Ohnuki et al., 1985, J. Bacteriol. 161(3):1010-1016.
Distler et al., 1985, FEMS Microbiology Letters 30:151-154.
Vara et al., 1985, Gene 33:197-206.
Birmingham et al., 1984, Abstracts of the ASM Conference on Genetics and Molecular Biology of Industrial Microorganisms, Bloomington, Ind., Abstract No. 220.
Uchiyama and Weisblum, 1985, Gene 38:103-110.
Barany et al., *J. Bacteriology*, 144 698 (1980).
Stonesifer et al., *Mol. Gen. Genet.* 202 348 (1986).

*Primary Examiner*—Thomas G. Wiseman
*Assistant Examiner*—Joan Ellis
*Attorney, Agent, or Firm*—Ron K. Levy; Leroy Whitaker

[57] ABSTRACT

The tlrC gene is a novel tylosin resistance-conferring gene isolated from Streptomyces fradiae and used to construct a number of cloning vectors for use in Streptomyces. One such cloning vector, plasmid pSKC10, can be obtained in *S. fradiae* JS87 under the accession number NRRL 18072. *S. fradiae* JS87 is the preferred host when the tlrC gene is used to select tylosin-resistant Streptomyces transformants.

25 Claims, 18 Drawing Sheets

Restriction Site and Function Map of
Plasmid pSKC10
(8.6 kb)

Restriction Site and Function Map of
Plasmid pSKC10
(8.6 kb)

Restriction Site and Function Map of
Plasmid pSKCAA
(8.45 kb)

Restriction Site and Function Map of
Plasmid pHJL289
(8.6 kb)

Restriction Site and Function Map of
Plasmid pSKC11
(10.9 kb)

Restriction Site and Function Map of
Plasmid pSVB49
(28.6 kb)

Restriction Site and Function Map of
Plasmid pSKCEE
(27.6 kb)

Restriction Site and Function Map of
Plasmid pIJ941
(24.8 kb)

Restriction Site and Function Map of
Plasmid pSVB48
(27.5 kb)

Restriction Site and Function Map of
Plasmid pSVB2
(10.55 kb)

Restriction Site and Function Map of
Plasmid pSVB9
(10.7 kb)

Restriction Site and Function Map of
Plasmid pSVB25
(8.7 kb)

Restriction Site and Function Map of
Plasmid pSVB36
(11.6 kb)

Restriction Site and Function Map of
Plasmid pSVB51
(14.4 kb)

Restriction Site and Function Map of
Plasmid pSVB37
(11.6 kb)

Restriction Site and Function Map of
Plasmid pSVB53
(14.4 kb)

Restriction Site and Function Map of
Plasmid pSVB55
(4.7 kb)

Restriction Site and Function Map of
Plasmid pSVB56
(7.4 kb)

Restriction Site and Function Map of
Plasmid pSVB59
(33.3 kb)

4,889,809

TYLOSIN RESISTANCE-CONFERRING GENE, DESIGNATED TLRC, FOR USE IN *STREPTOMYCES FRADIAE*

SUMMARY OF THE INVENTION

The present invention comprises a novel tylosin resistance-conferring gene, designated tlrC, recombinant DNA cloning vectors that comprise the novel gene, and transformants containing the tylosin resistance-conferring vectors. *Streptomyces fradiae* produces tylosin, used in veterinary medicine as an animal growth promotant and antibiotic. Tylosin is a macrolide antibiotic consisting of a 16-member cyclic lactone and three sugar residues. The antibiotic activity of tylosin, like other macrolides, is due to inhibition of protein synthesis by a mechanism that involves the binding of tylosin to the ribosome.

The present invention provides tylosin resistance-conferring cloning vectors for use in *Streptomyces fradiae*. The development and exploitation of recombinant DNA technology in Streptomyces depends upon the availability of selectable genetic markers on suitable cloning vectors. This development has been somewhat retarded by the low number of selectable markers presently available for use in Streptomyces. The present invention is useful and especially important in that it expands the number of selectable markers suitable for usch use.

The vectors of the present invention are particularly useful, because the vectors are small, versatile, and can be transformed and selected in a variety of tylosin-sensitive *Streptomyces fradiae* strains, such as strain JS87. Streptomyces provides over half of the clinically important antibiotics and thus is a commercially significant group. The present invention provides new and useful cloning systems and vectors for this industrially important group and allows for the cloning of genes both for increasing the yields of known antibiotics and also for producing new antibiotics and antibiotic derivatives.

The present invention further provides vectors that enable selection of Streptomyces transformants from a background of untransformed cells. After the addition of non-selectable DNA to a vector of the present invention, the modified vector can be transformed into *Streptomyces fradiae* and transformants selected by their tylosin-resistant phenotype. Because transformation is a relatively low frequency event, such a functional test is a practical necessity for determining which cell(s), of among the millions of cells, has acquired the transforming DNA.

For purposes of the present invention, as disclosed and claimed herein, the following terms are defined below.

ApR—the ampicillin-resistant phenotype or gene conferring same.

mel—the tyrosinase gene.

Phasmid—a recombinant DNA vector that may act as a phage or as a plasmid.

Recombinant DNA Cloning Vector—any autonomously replicating or integrating agent, including, but not limited to, plasmids, comprising a DNA molecule to which one or more additional DNA segments can be or have been added.

Restriction Fragment—any linear DNA molecule generated by the action of one or more restriction enzymes.

Sensitive Host Cell—a host cell that cannot grow in the presence of a given antibiotic without a DNA segment that provides resistance thereto.

TcR—the tetracycline-resistant phenotype or gene conferring same.

tlrA—a tylosin resistance-conferring gene of type A.
tlrB—a tylosin resistance-conferring gene of type B.
tlrC—a tylosin resistance-conferring gene of type C.

Transformant—a recipient host cell that has undergone transformation.

Transformation—the introduction of DNA into a recipient host cell that changes the genotype and results in a change in the recipient cell.

tsrR—the thiostrepton-resistant phenotype or gene conferring same.

tyl—a tylosin biosynthetic gene.

BRIEF DESCRIPTION OF THE FIGURES

The FIGURES described below are drawn to scale. For some restriction enzymes, such as SauIIIA1, only the significant cut sites are shown.

DETAILED DESCRIPTION OF THE INVENTION

The present invention concerns a novel tylosin resistance-conferring gene, designated tlrC, that is useful as a selectable marker in *Streptomyces fradiae*. The tlrC gene can be isolated from plasmid pSKC10 on an ~2.8 kb BamHI restriction fragment; plasmid pSKC10 can be isolated from *Streptomyces fradiae* JS87/pSKC10, a strain deposited and made part of the permanent culture collection of the Agricultural Research Service, Northern Regional Research Center (NRRL), Peoria, Ill. 61604, under the accession number NRRL 18072. A pHJL315, one obtains useful plasmids of the present invention, as depicted in Table II.

TABLE II

Figure 1:
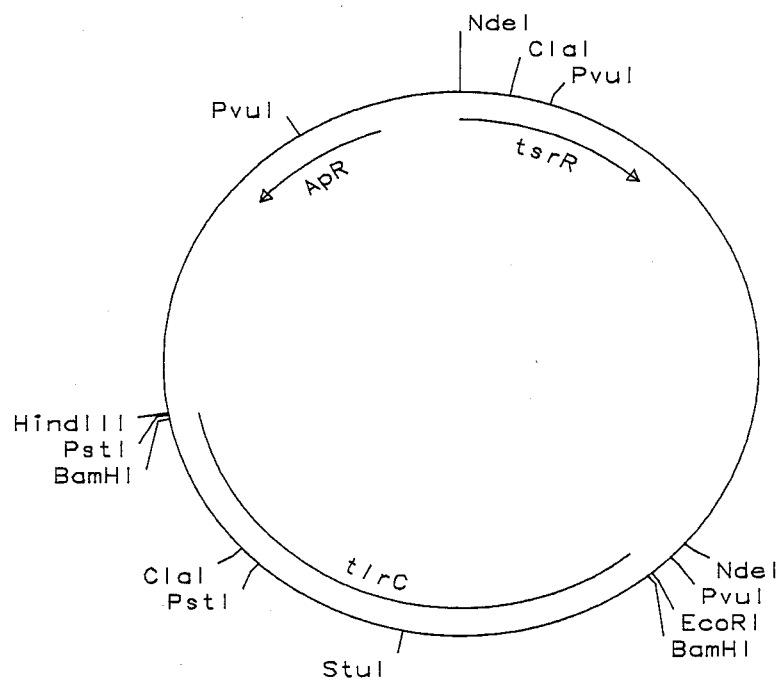
FIG. 1 is a restriction site and function map of plasmid pSKC10.

| Ligation | Plasmids Produced | Description |
|---|---|---|
| Eco-RI-digested plasmid pSKC10 and the ~15.7 kb EcoRI restriction fragment of plasmid pHJL280 | pSKC30 pSKC31 | In plasmid pSKC30, the tylE gene is adjacent to the tlrC gene; plasmid pSKC31 is the opposite orientation. |
| Eco-RI-digested plasmid pSKC10 and the ~17 kb EcoRI restriction fragment of plasmid pHJL284 | pSKC32 pSKC33 | In plasmid pSKC32, the tylF gene is adjacent to the tlrC gene; plasmid pSKC33 is the opposite orientation. |
| Eco-RI-digested plasmid pSKC10 and the ~18.5 kb EcoRI restriction fragment of plasmid pHJL309 | pSKC34 pSKC35 | In plasmid pSKC34, the tylL gene is adjacent to the tlrC gene; plasmid pSKC35 is the opposite orientation. |
| Eco-RI-digested plasmid pSKC10 and the ~19.6 kb EcoRI restriction fragment of plasmid pHJL2311 | pSKC36 pSKC37 | In plasmid pSKC36, the tylH gene is adjacent to the tlrC gene; plasmid pSKC37 is the opposite orientation. |
| Eco-RI-digested plasmid pSKC10 and the ~33 kb EcoRI restriction fragment of plasmid pHJL315 | pSKC38 pSKC39 | In plasmid pSKC38, the tylE gene is adjacent to the tlrC gene; plasmid pSKC39 is the opposite orientation. | restriction site and function map of plasmid pSKC10 is presented in FIG. 1 of the accompanying drawings. Plasmid pSKC10 can be isolated from S. fradiae JS87/pSKC10 in substantial accordance with the procedure described in Example 1.

Figure 2:
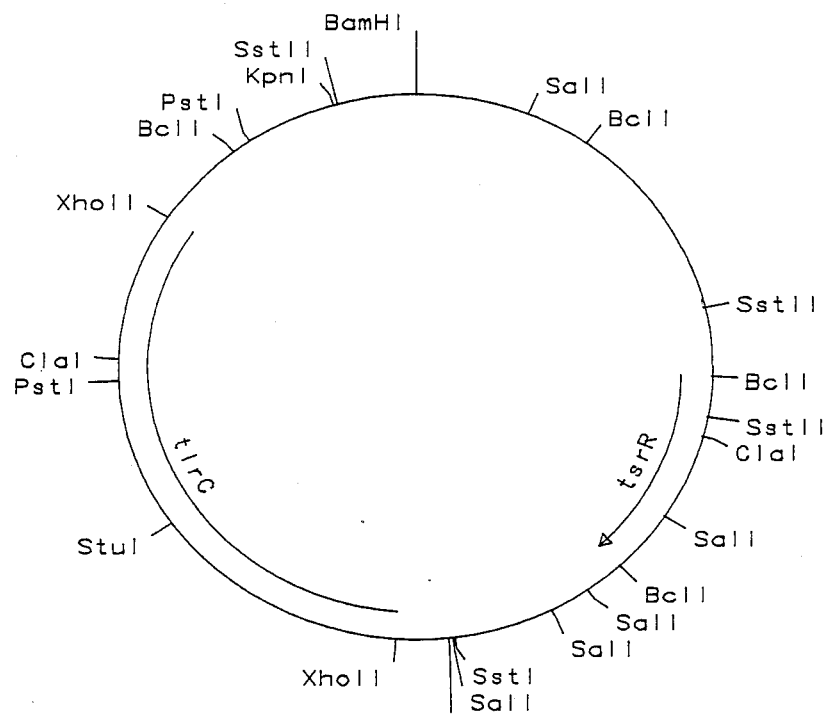
FIG. 2 is a restriction site and function map of plasmid pSKCAA.

Plasmid pSKC10 serves as useful starting material for the construction of other vectors that confer tlrC-mediated tylosin resistance. For example, the ~2.8 kb BamHI, tylosin resistance-conferring restriction fragment of plasmid pSKC10 can be isolated and inserted into BglII-digested plasmid pIJ702 (ATCC 39155) to yield plasmids pSKCAA and pSKCBB, which differ only with respect to the orientation of the tlrC-containing, BamHI restriction fragment. The construction protocol for plasmids pSKCAA and pSKCBB is given in Example 2; a restriction site and function map of plasmid pSKCAA is presented in FIG. 2 of the accompanying drawings.

The tlrC gene can also be inserted into a variety of vectors that encode one or more important enzymes in the tylosin biosynthetic pathway. U.S. patent application No. 07/018,237, filed Feb. 24, 1987, is a continuation-in-part of U.S. patent application No. 890,670, filed July 25, 1986, now abandoned, which is a continuation-in-part of U.S. patent application Ser. No. 842,330, filed Mar. 21, 1986, now abandoned incorporated herein by reference, describes a number of vectors that encode key enzymes in the tylosin biosynthetic pathway. Table I, below, describes these plasmids and provides the accession number by which the plasmids can be obtained.

TABLE I

| Plasmids Comprising Tylosin Biosynthetic Genes | | |
|---|---|---|
| Host Designation | Tylosin Gene(s) | NRRL Accession No. |
| E. coli K12 HB101/pHJL280 | D, E, F, H, J | B-18043 |
| E. coli K12 HB101/pHJL284 | C, F, J | B-18044 |
| E. coli K12 HB101/pHJL309 | L, M | B-18045 |
| E. coli K12 HB101/pHJL311 | C, F, J, K, H | B-18046 |
| E. coli K12 JM109/pHJL315 | D, E, F, H, J | B-18047 |

Figure 3:
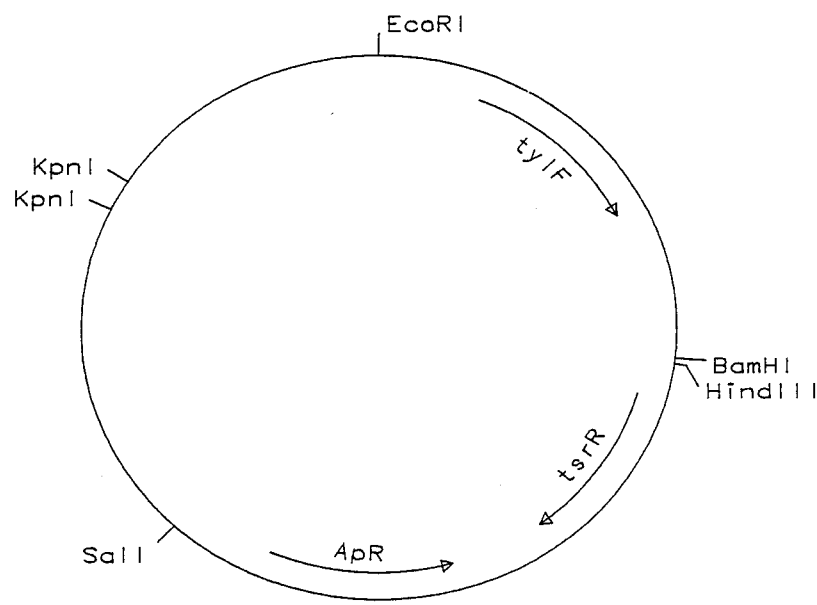
FIG. 3 is a restriction site and function map of plasmid pHJL289.
Figure 4:
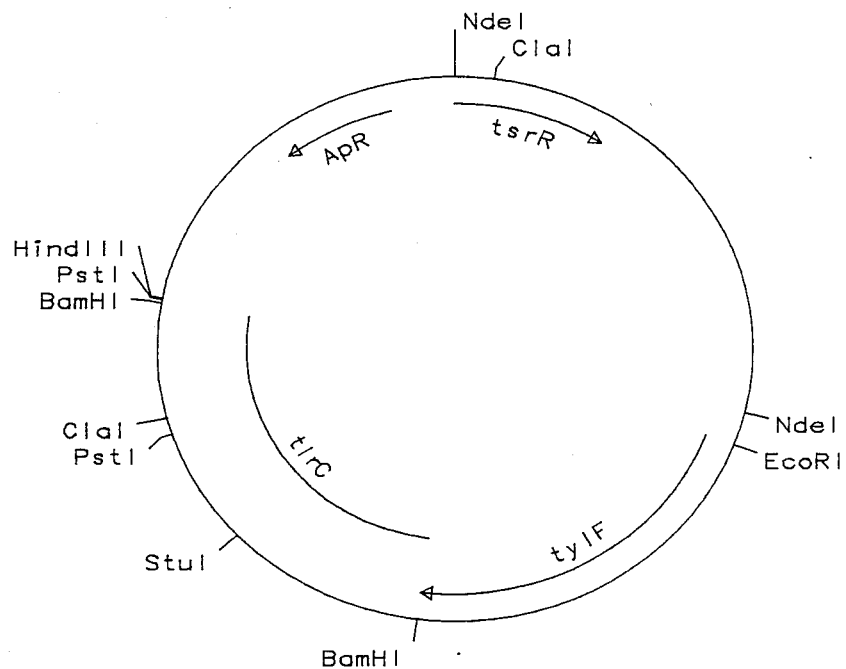
FIG. 4 is a restriction site and function map of plasmid pSKC11.

The tylosin bissynthetic genes are linked in the order: E, D, H, F, J, C, K, and L and M. The tylosin biosynthetic gene-containing DNA of each of plasmids pHJL280, pHJL284, EcoRI restriction fragment. By ligating EcoRI-digested plasmid pSKC10 with the tylosin biosynthetic gene-containing, EcoRI restriction fragment of plasmid pHJL280, pHJL284, pHJL308, pHJL311, or Plasmid pHJL289 encodes macrocin-O-methyltransferase, the tylF gene product, and was disclosed in Table XII of Serial No. 842,330. A restriction site and function map of plasmid pHJL289 is presented in FIG. 3 of the accompanying drawings, and the construction protocol for plasmid pHJL289 is presented in Example 3. The ~2.8 kb tlrC-containing, BamHI restriction fragment of plasmid pSKC10 was inserted into BamHI-digested plasmid pHJL289 to yield plasmids pSKC11 and pSKC12. A restriction site and function map of plasmid pSKC11 is presented in FIG. 4 of the accompanying drawings; the construction protocol for plasmid pSKC11 is presented in Example 3.

Figure 5:
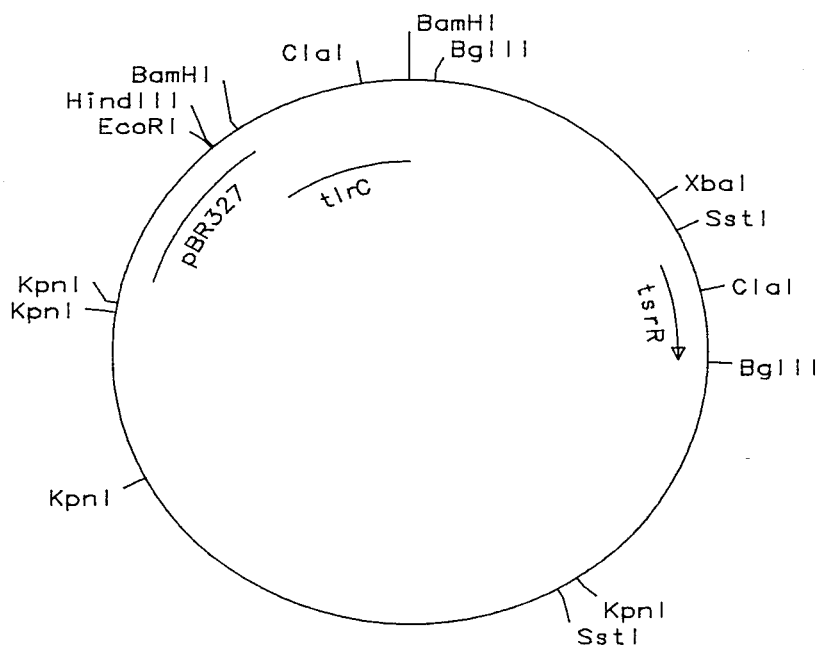
FIG. 5 is a restriction site and function map of plasmid pSVB49.

The tlrC gene can be used to construct vectors that have a low copy number in Streptomyces. The ~2.8 kb, tlrC-containing BamHI restriction fragment of plasmid pSKC10 can be inserted into BamHI-digested plasmid pIJ903 to yield plasmids psVB49 and pSVB50, which differ only with respect to the orientation of the inserted fragment. Plasmid pIJ903 was disclosed in Lydiate et al., 1985, Gene 35:223–235, and is commercially available from the John Innes Streptomyces Culture Collection (JICC), John Innes Institute, Colney Lane, Norwich, England NR4-7UH, under the accession number 3417. Plasmid pIJ903 has a copy number of about 1 in Streptomyces; plasmids pSVB49 and pSVB50 have a similar copy number. A restriction site and function map of plasmid pSVB49 is presented in FIG. 5 of the accompanying drawings. The construction protocol for plasmids pSVB49 and pSVB50 is presented in Example 4.

Figure 6:
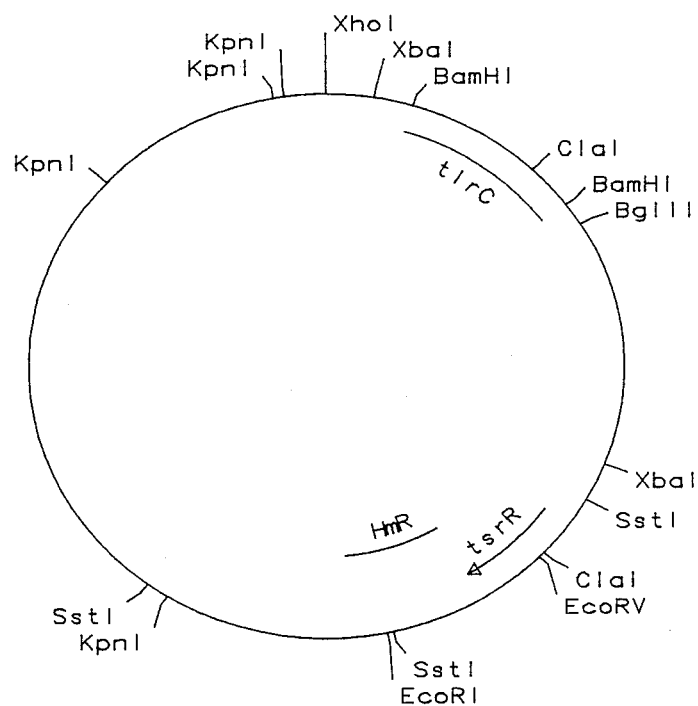
FIG. 6 is a restriction site and function map of plasmid pSKCEE.

The tlrC gene can be inserted into plasmid pIJ941 to yield two useful Streptomyces vectors designated pSKCEE and pSKCFF. Plasmid pIJ941 is commercially available from the JICC under the accession number 3338. Plasmids pSKCEE and pSKCFF are constructed by ligating the ~2.8 kb, tlrC-containing BamHI restriction fragment of plasmid pSKC10 into BamHI-digested plasmid pIJ941. The construction protocol for plasmids pSKCEE and pSKCFF is presented in Example 5. A restriction site and function map of plasmid pSKCEE is presented in FIG. 6 of the accompanying drawings.

Other illustrative plasmids of the present invention are constructed by inserting the ~2.8 kb tlrC-containing, BamHI restriction fragment of plasmid pSKC10 into a plasmid pIJ941 derivative. This derivative, designated plasmid pSVB34, was constructed by digesting plasmid pIJ941 with restriction enzymes EcoRV and ClaI, treating with Klenow, and self-ligating the resulting fragment. These manipulations inactivated the thiostrepton resistance-conferring gene, so plasmid pSVB34 does not confer thiostrepton resistance. Plasmid pSVB34 is then digested with restriction enzyme BamHI and ligated to the ~2.8 kb, tlrC-containing BamHI restriction fragment of plasmid pSKC10 to yield plasmids pSVB48 and pSVB57, which differ only with respect to the orientation of the ~2.8 kb BamHI restriction fragments. Restriction site and function maps of plasmids pIJ941 and pSVB48 are respectively presented in FIGS. 7 and 8 of the accompanying drawings. The construction protocol for plasmids pSVB34, pSVB48, and pSVB57 is presented in Example 5.

Although many of the plasmids illustrative of the present invention were constructed by inserting the ~2.8 kb, tlrC-containing restriction fragment of plasmid pSKC10 into a cloning vector, restriction fragments used to construct vectors illustrative of the present invention can be conventionally modified to facilitate ligation. For example, molecular linkers can be provided to a particular tlrC gene-containing restriction fragment or to DNA comprising vector replication or integration functions. Thus, specific sites for subsequent ligation can be conveniently constructed. In addition, the various tlrC gene-containing restriction fragments, origin of replication, or integration sequences of a given vector can be modified by adding, eliminating, or substituting certain nucleotides to alter characteristics and to provide a variety of restriction sites for ligation of DNA. Those skilled in the art understand nucleotide chemistry and the genetic code and thus which nucleotides are interchangeable and which DNA modifications are desirable for a specific purpose. It is also noteworthy that a given tylosin resistance gene-containing restriction fragment is not limited to a particular position on a cloning vector, as long as critical, vector-controlled functions are not disrupted. Those skilled in the art understand or can readily determine which sites on a vector are advantageous for the ligation or insertion of a particular tylosin resistance gene-containing restriction fragment.

The tlrC gene was isolated from a tylosin-producing strain of Streptomyces fradiae. In the isolation procedure, genomic DNA of S. fradiae was partially digested with restriction enzyme SauIIIA1, and the resulting DNA was inserted into BglII-digested plasmid pIJ702 to yield a number of tlrC-containing plasmids, including plasmid pSKC9. Plasmid pSCK9 was then digested with restriction enzyme BamHI, and the ~2.8 kb, tylosin resistance-conferring BamHI restriction fragment of plasmid pSKC9 was ligated to BamHI-digested plasmid pHJL401 to yield plasmid pSKC10. Because the tlrC gene was isolated from S. fradiae, the tlrC gene functions in S. fradiae. However, tylosin-producing Streptomyces strains are naturally resistant to tylosin (in part due to the presence of a tlrC gene); therefore, a plasmid containing only the tlrC gene cannot be readily selected for in a tylosin-producing Streptomyces strain. Furthermore, the tlrC gene is not sufficient to confer tylosin resistance to many non-S. fradiae streptomycetes. The mechanism of action of tlrC-mediated tylosin resistance is not known; the tlrC gene product may positively regulate the expression of the tlrA and tlrB tylosin resistance-conferring genes of S. fradiae.

The tlrA and tlrB tylosin resistance-conferring genes were respectively disclosed and claimed in U.S. patent application Ser. No. 653,975, filed Sept. 25, 1984 and U.S. patent application Ser. No. 871,051, filed June 5, 1986. The tlrC gene may positively regulate tlrA and tlrB expression, because Streptomyces fradiae JS87, a tylosin-sensitive, tylosin-deficient mutant of a tylosin-producing S. fradiae strain, contains what seem to be intact copies of the tlrA and tlrB genes yet lacks a tlrC gene. Introduction of the tlrC gene into S. fradiae JS87, as by transformation with plasmid pSKC10, restores tylosin resistance to the mutant strain. Thus, S. fradiae JS87, which can be isolated from S. fridiae JS87/pSKC10 (NRRL 18072) by the procedure of Example 6, is the preferred host for the plasmids of the present invention when tlrC is to serve as a selectable marker that confers tylosin resistance. The tlrA gene does not confer tylosin resistance to S. fradiae JS87 in the absence of tlrC, and the tlrB gene will confer tylosin resistance to JS87 in the absence of tlrC only if present in high copy number.

The intact tlrC gene is useful to confer tylosin resistance, and the various components of the tlrC gene can be isolated by recombinant DNA techniques and used for a variety of purposes in a wide range of streptomycete strains. Plasmid pSKC10 contains the complete tlrC gene: (1) a promoter that directs transcription of the protein-coding sequence; (2) a sequence that, when transcribed into mRNA, directs translation of the transcript; (3) a protein-coding sequence; and (4) a transcription terminator. Each of these elements is independently useful and can, through the techniques of recombinant DNA technology, be used to form recombinant genes of great variety. DNA sequencing of the ~2.8 kb BamHI restriction fragment of plasmid pSKC10 will reveal the precise location of the tlrC coding sequence and thus allow one to position other promoters in reading phase with the tlrC coding sequence. By choosing the proper promoter, one can construct vectors that drive expression of the tlrC gene product in any given host cell. The promoter of the tlrC gene is useful in its own right. The promoter and other regulatory elements of the tlrC gene can be linked to the coding sequence of a non-tylosin antibiotic biosynthetic gene to prepare a hybrid gene that functions in Streptomyces fradiae to yield a hybrid antibiotic. Thus, the individual elements of the gene on the plasmids described herein comprise important components of the present invention.

The present invention comprises recombinant vectors that contain the tlrC gene, or portions of the tlrC gene, and are useful to elucidate the structure of the tlrC gene. Plasmid pSP64 (available from Promega Biotec, 2800 South Fish Hatchery Road, Madison, Wis. 53711) is a riboprobe vector that can be modified and then used to prepare tlrC messenger RNA. Plasmid pSP64 was digested with restriction enzyme BamHI and ligated to the ~2.8 kb, tlrC-containing BamHI restriction fragment of plasmid pSKC10 to yield plasmids pHDM101 and pHDM102, which differ only with respect to the orientation of the tlrC-containing restriction fragment. Plasmids pHDM101 and pHDM102 are useful in determining the direction of transcription of the tlrC gene and the nucleotide sequence of the tlrC gene and in delineating the boundaries of the tlrC coding sequence. Thus, plasmids pHDM101 and pHDM102 can be used to generate information necessary for genetic engineering involving the various components of the tlrC gene.

Although the present invention is not limited by the theory of the mechanism of action of the tlrC gene product, it is believed that the tlrC gene product regulates tlrA and tlrB gene expression. Thus, the intact tlrC gene can be used in Streptomyces species other than *S. fradiae* JS87 as a potentiator of tlrA and/or tlrB-mediated tylosin resistance. The tlrB gene does not confer tylosin resistance to *S. griseofuscus* yet does confer tylosin resistance to *S. lividans*. The observations, which support the theory of the mechanism of action of the tlrC gene product, described above concerning the tlrA, tlrB, and tlrC genes in *S. fradiae* JS87 suggest that tlrB will confer tylosin resistance to *S. griseofuscus* in the presence of the tlrC gene product. The tlrA, tlrB, and tlrC genes can be combined in a variety of ways on recombinant vectors, thus allowing for the construction of vectors which confer resistance in a variety of Streptomyces species.

Figure 9:
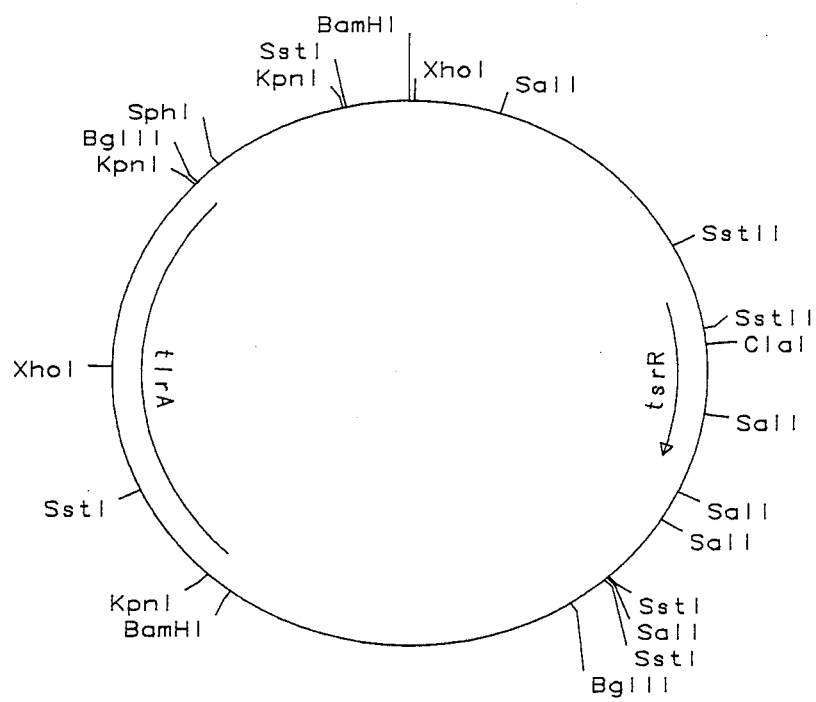
FIG. 9 is a restriction site and function map of plasmid pSVB2.
Figure 10:
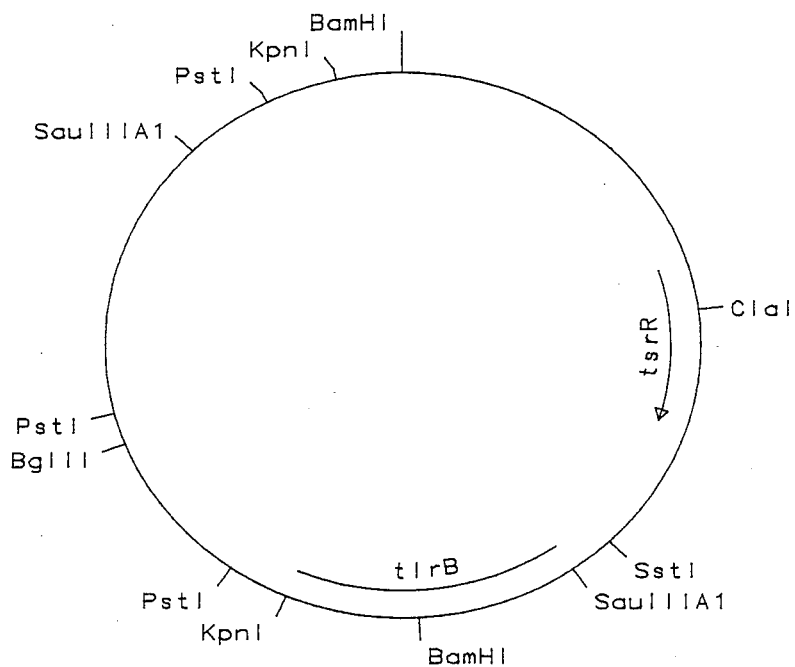
FIG. 10 is a restriction site and function map of plasmid pSVB9.

The tlrA gene can be isolated from plasmid pSVB2, which can be obtained from *Streptomyces lividans* TK23/pSVB2, available from the NRRL under the accession number NRRL 15880. A restriction site and function map of plasmid pSVB2 is presented in FIG. 9 of the accompanying drawings. The tlrB gene can be isolated from plasmid pSVB9, which can be obtained from *Streptomyces lividans* TK23/pSVB9, available from the NRRL under the accession number NRRL 18073. A restriction site and function map of plasmid pSVB9 is presented in FIG. 10 of the accompanying drawings. U.S. patent application Ser. No. 871,051, filed June 5, 1986, discloses and claims plasmid pSVB25, a derivative of the tlrB-containing plasmid pSVB9. Plasmid pSVB25 was used to construct plasmids, designated pSVB36 and pSVB37, which contain both the tlrA and tlrB genes. The construction protocol for plasmids pSVB25, pSVB36, and pSVB37 is presented in Example 7.

Figure 13:
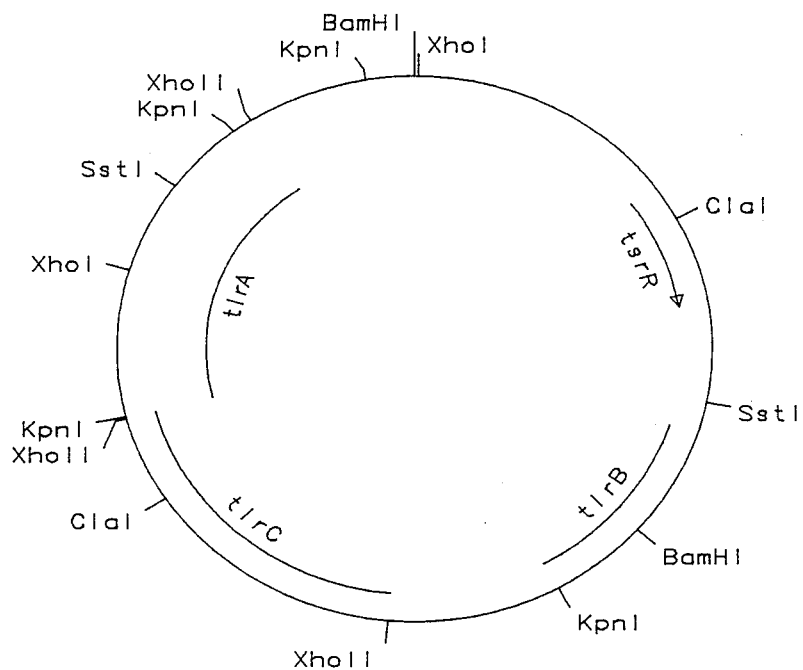
FIG. 13 is a restriction site and function map of plasmid pSVB51.

Plasmids pSVB36 and pSVB37 can be modified to illustrate that the present invention comprises expression vectors that contain the tlrC gene and either the tlrA gene or the tlrB gene or both the tlrA and tlrB genes. Plasmid pSVB36 is digested with restriction enzyme BglII, and the ~2.8 tlrC gene-containing BamHI restriction fragment of plasmid pSKC10 is inserted to yield plasmids pSVB51 and pSVB52, which differ only with respect to the orientation of the inserted tlrC-containing restriction fragment. The construction protocol for plasmids pSVB51 and pSVB52 is presented in Example 7; a restriction site and function map of plasmid pSVB51 is presented in FIG. 13 of the accompanying drawings.

Figure 14:
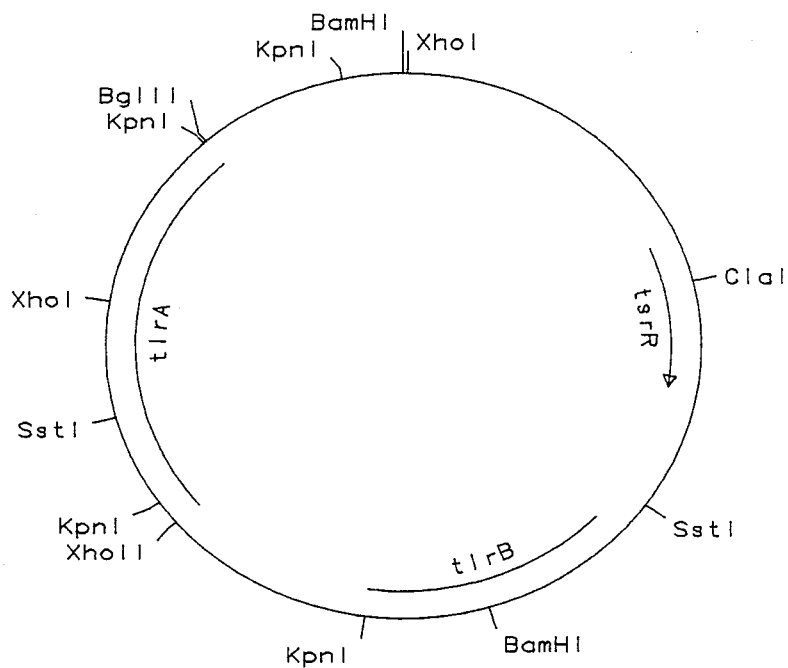
FIG. 14 is a restriction site and function map of plasmid psVB37.
Figure 15:
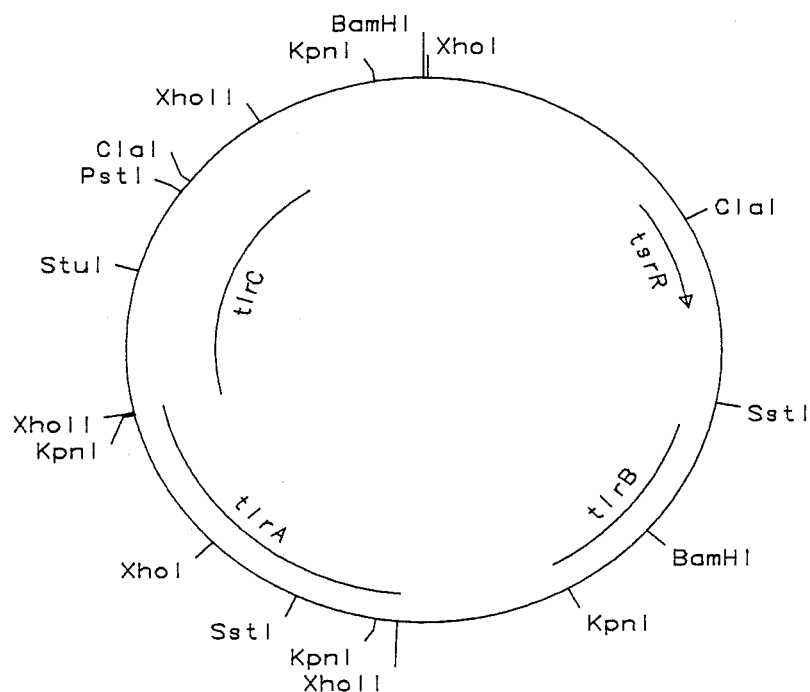
FIG. 15 is a restriction site and function map of plasmid pSVB53.

As also described in Example 7, plasmid pSVB37, which differs from plasmid pSVB36 only with respect to the orientation of the ~2.9 kb, tlrA gene-containing BamHI-BglII restriction fragment, can likewise be digested with restriction enzyme BglII and ligated to the ~2.8 kb, tlrc gene-containing BamHI restriction fragment of plasmid pSKC10. This ligation produces plasmids pSVB53 and pSVB54, which differ only with respect to the orientation of the tlrC gene-containing restriction fragment. Restriction site and function maps of plasmids pSVB37 and pSVB53 are respectively presented in FIGS. 14 and 15 of the accompanying drawings.

Figure 16:
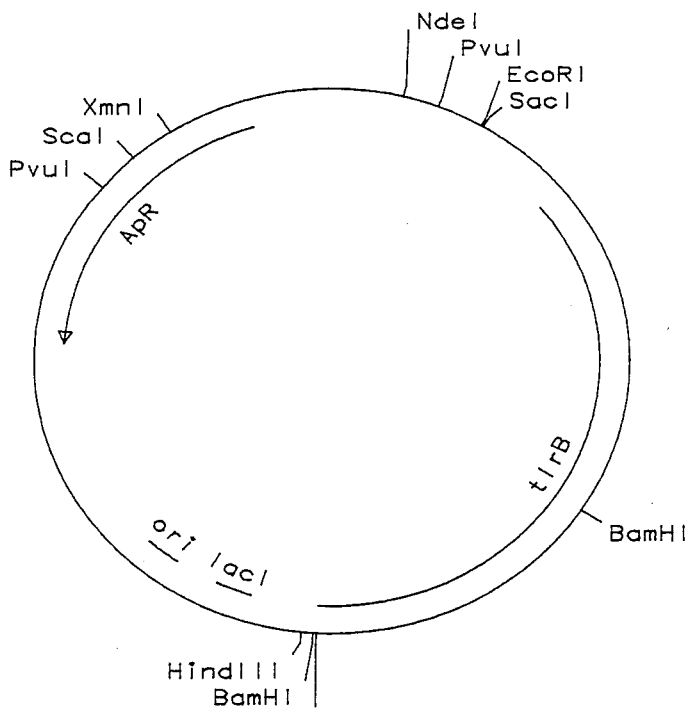
FIG. 16 is a restriction site and function map of plasmid pSVB55.

Other illustrative plasmids of the present invention that comprise the tlrA, tlrB, and tlrC genes can be constructed by ligating the ~2.0 kb, tlrB-containing SacI-KpnI restriction fragment of plasmid pSVB25 to SacI-Kpn-digested plasmid pUC19 (ATCC 37254) to yield plasmid pSVB55. A restriction site and function map of plasmid pSVB55 is presented in FIG. 16 of the accompanying drawings. Plasmid pSVB55 is then digested with restriction enzyme KpnI and ligated to the ~2.67 kb, tlrA-containing KpnI restriction fragment of plasmid pSVB2 to yield plasmids pSVB56 and pSVB58, which differ only with respect to the orientation of the tlrA-containing restriction fragment.

Figure 17:
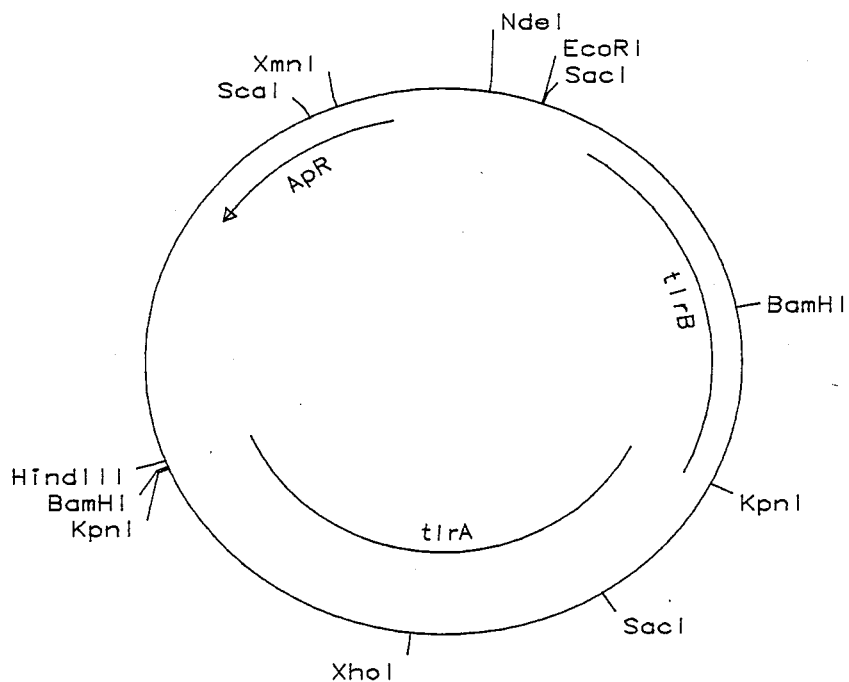
FIG. 17 is a restriction site and function map of plasmid pSVB56.
Figure 18:
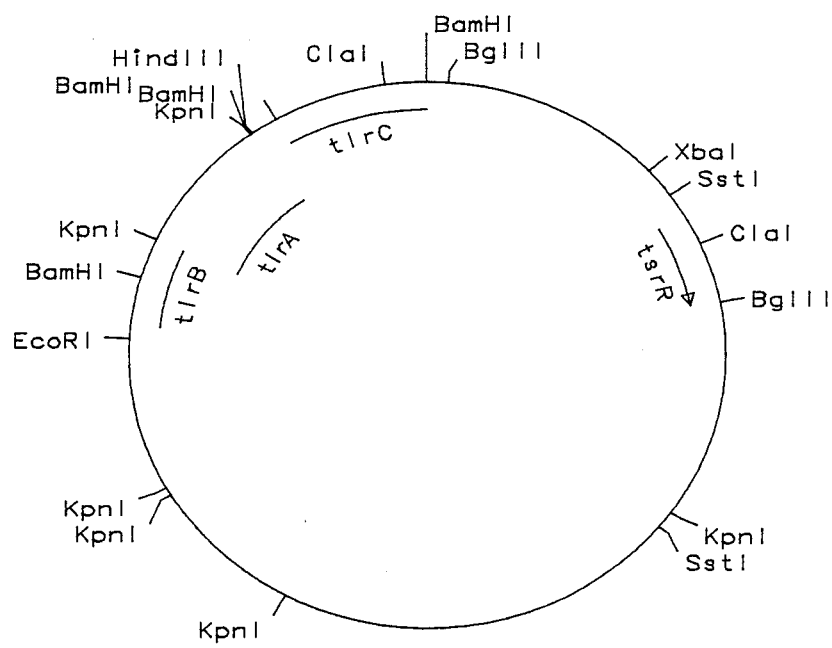
FIG. 18 is a restriction site and function map of plasmid pSVB59.

The tlrA-tlrB-containing, ~4.7 kb EcoRI-HindIII restriction fragment of plasmid pSVB56 can be ligated to the large EcoRI-HindIII restriction fragment of plasmid pSVB49 to yield plasmid pSVB59. The tlrA-tlrB-containing ~4.7 kb EcoRI-HindIII restriction fragment of plasmid pSVB56 can be ligated to the large EcoRI-HindIII restriction fragment of plasmid pSVB50 to yield plasmid pSVB60. The tlrA-tlrB-containing ~4.7 kb EcoRI-HindIII restriction fragment of plasmid pSVB58 can also be ligated to the large EcoRI-HindIII restriction fragment of plasmid pSVB49 to yield plasmid pSVB61. The tlrA-tlrB-containing 4.7 kb EcoRI-HindIII restriction fragment of plasmid pSVB58 is ligated to the large EcoRI-HindIII restriction fragment of plasmid pSVB50 to yield plasmid pSVB62. Plasmids pSVB59, pSVB60, pSVB61, and pSVB62 each comprise the tlrA, tlrB, and tlrC genes. Restriction site and function maps of plasmids pSVB56 and pSVB59 are respectively presented in FIGS. 17 and 18 of the accompanying drawings. The construction protocol for plasmids pSVB59, pSVB60, pSVB61, and pSVB62 is described in Example 9.

Although the above-described vectors of the present invention comprise the Streptomyces replicon derived from such plasmids as pIJ702, pIJ903, pIJ941, a variety of known Streptomyces replicons can be used to construct equally useful vectors with different host ranges. Table III is an illustrative, but not comprehensive, listing of Streptomyces plasmids from which Streptomyces replicons can be obtained. Those skilled in the art recognize that, so long as the replicon function is not disrupted, all or part of the plasmids listed in the Table may be used to construct vectors that contain the tlrC gene of the present invention. The plasmid-containing host and depository accession number are also listed in Table III.

TABLE III

| Streptomyces Plasmids | | |
|---|---|---|
| Plasmid | Host | Accession Number |
| SCP2 | *Streptomyces coelicolor* A3(2) | NRRL 15042 |
| SCP2* | *Streptomyces coelicolor* M110 | NRRL 15041 |
| pEL7 | *Streptomyces ambofaciens*/pEL7 | NRRL 12523 |
| pUC6 | *Streptomyces espinosus* | NRRL 11439 |
| pUC3 | Streptomyces 3022A | NRRL 11441 |
| SLP1 | *Streptomyces lividans* | NCIB* 11417 |
| pNM100 | *Streptomyces virginiae* | NRRL 15156 |
| pEL103 | *Streptomyces granuloruber* A399 12.13/pEL103 | NRRL 12549 |
| pIJ702 | *Streptomyces lividans* | ATCC** 39155 |

*National Collection of Industrial Bacteria (NCIB), Torry Research Station, Post Office Box 31, 135 Abbey Road, Aberdeen AB98DG, Scotland, United Kingdom.
**American Type Culture Collection, Rockville, MD 20852.

Of course, the tlrC gene can be used to construct vectors other than plasmids. Phage φC31 is a well-known Streptomyces phage that is an excellent source of starting material for constructing integrative tylosin resistance-conferring vectors that further exemplify the present invention. A derivative of phage φC31, phasmid pKC331, is especially preferred for constructing such integrating vectors and can be obtained from *E. coli* K12 BE447/pKC331 (NRRL B-15828). φC31-type phages are integrative vectors and can be readily modified to incorporate the tlrC gene and thus serve as a vector for integrating the tlrC gene into the Streptomyces genome.

The vectors of the present invention comprise a Streptomyces replicon and a tylosin resistance-conferring restriction fragment. Because amplification and manipulation of plasmids is done faster and more efficiently in *E. coli* than in Streptomyces, it is convenient to add DNA sequences that also allow for replication in *E. coli*. Thus, the addition of functional replicon-containing and antibiotic resistance-conferring restriction fragments from *E. coli* plasmids such as, for example, pBR322, pACYC184, pBR325, pBR328, and the like is highly advantageous and adds to the general utility of the present illustrative vectors.

The vectors used in the present method confer tylosin resistance to the preferred strain, *Streptomyces fradiae* JS87. Although 10 µg/ml of tylosin is generally toxic to *Streptomyces fradiae* JS87 and most other tylosin-sensitive Streptomyces strains, the vectors of the present invention confer resistance to levels approaching 2 mg/ml of tylosin. The preferred tylosin concentration for purposes of selecting tlrC-containing transformants, however, is about 500 µg/ml for *Streptomyces fradiae* JS87.

The recombinant DNA cloning vectors of the present invention have broad utility and help fill the need for suitable cloning vehicles for use in Streptomyces and related organisms. Moreover, the ability of the present vectors to confer tylosin resistance provides a functional means for selecting transformants. This is important because of the practical necessity for determining and selecting the particular cells that have acquired vector DNA in a transformation procedure.

Additional DNA segments, that lack functional tests for their presence, can also be inserted into the present vectors, and transformants containing the non-selectable DNA can be isolated by selection for tylosin resistance. Such non-selectable DNA segments can be inserted at any site, except within regions necessary for plasmid function and replication or within the tlrC gene, and include, but are not limited to, genes that specify antibiotic modification enzymes and regulatory genes of all types.

More particularly, a non-selectable DNA segment that comprises a gene is inserted into a plasmid such as, for example, plasmid pSKC10 at the central ClaI restriction site of the thiostrepton resistance-conferring gene. Such an insertion inactivates the thiostrepton resistance-conferring gene and thus allows for the easy identification of transformants containing the recombinant plasmid. This is done by first selecting for tylosin resistance and, secondarily, identifying those tylosin-resistant transformants that are not resistant to thiostrepton. Therefore, the ability to select for tylosin resistance in Streptomyces and related cells allows for the efficient isolation of the extremely rare cells that contain the particular non-selectable DNA of interest.

The functional test for tylosin resistance, described above, is also used to locate DNA segments that act as control elements and direct expression of an individual antibiotic resistance gene. Such segments, including, but not limited to, promoters, attenuators, repressors, inducers, ribosome-binding sites, and the like, are used to control the expression of other genes in Streptomyces and related organisms.

The tylosin resistance-conferring vectors of the present invention are also useful for ensuring that linked DNA segments are stably maintained in host cells over many generations. These genes or DNA fragments, covalently linked to the tylosin resistance-conferring DNA and propagated in Streptomyces, are maintained by exposing the transformants to levels of tylosin toxic to non-transformed cells. Therefore, transformants that lose the vector, and consequently lose any covalently linked DNA, cannot grow and are eliminated from the culture. Thus, the vectors of the present invention can stabilize and maintain any DNA sequence of interest.

The cloning vectors and transformants of the present invention provide for the cloning of genes to improve yields of various products that are currently produced in Streptomyces and related cells. Examples of such products include, but are not limited to, streptomycin, tylosin, cephalosporins, actaplanin, narasin, monensin, tobramycin, erythromycin, and the like. The present invention also provides selectable vectors that are useful for cloning, characterizing, and reconstructing DNA sequences that code for: commercially important proteins such as, for example, human insulin, human proinsulin, glucagon, interferon and the like; enzymatic functions in metabolic pathways leading to commercially important processes and compounds; or control elements that improve gene expression. These desired DNA sequences also include, but are not limited to, DNA that codes for enzymes that catalyze synthesis of derivatized antibiotics such as, for example, streptomycin, cephalosporin, tylosin, actaplanin, narasin, monensin and erythromycin derivatives, or for enzymes that mediate and increase bioproduction of antibiotics or other products. The capability for isolating and using such DNA segments allows for increasing the yield and availability of antibiotics that are produced by Streptomyces and related organisms.

Streptomyces can be cultured in a number of ways using any of several different media. Preferred carbohydrate sources in a culture medium include, for example, molasses, glucose, dextrin, and glycerol. Nitrogen sources include, for example, soy flour, amino acid mixtures, and peptones. Nutrient inorganic salts are also incorporated and include the customary salts capable of yielding sodium, potassium, ammonium, calcium, phosphate, chloride, sulfate, and like ions. As is necessary for the growth and development of other microorganisms, essential trace elements are also added. Such trace elements are commonly supplied as impurities incidental to the addition of other constituents of the medium.

Streptomyces is grown under aerobic culture conditions over a relatively wide pH range of about 5 to 9 at temperatures ranging from about 15° to 40° C. For plasmid stability and maintenance, it is desirable to start with a culture medium at a pH of about 7.2 and maintain a culture temperature of about 30° C.

The following examples further illustrate and describe the invention disclosed herein. The invention is not limited in scope by reason of any of the following Examples; sources of reagents or equipment are provided merely for convenience and in no way limit the invention. Both an explanation of and the actual procedures for constructing the invention are described where appropriate.

EXAMPLE 1

Isolation of Plasmid pSKC10

A. Culture of *Streptomyces fradiae* JS87/pSKC10

A lyophilized culture of *Streptomyces fradiae* JS87/pSKC10 (NRRL 18072) is inoculated into 10 ml of TSB medium (Trypticase Soy Broth*) containing 20 μg/ml thiostrepton and grown at 29° C. until the culture was in early stationary phase (24–72 hours). The culture was then homogenized, and 5 ml of the homogenized culture were used to inoculate 100 ml of TSB also containing thiostrepton. The 100 ml of culture were incubated at 29° C. until the *Streptomyces fradiae* JS87/pSKC10 cells reached stationary phase.

*TSB is made at 30 g/l and is obtained from: Bethesda Research Laboratories (BRL), Inc., 8717 Grovemont Circle, P.O. Box 577, Gaithersburg, Md. 20760.

B. Plasmid Isolation

The cells were collected and washed once with a 10.3% sucrose solution. The cells were then suspended in 24 ml of 10.3% sucrose, to which 6 ml of 5X lysozyme solution (125 mM Tris-HCl, pH=8; 125 mM $Na_2EDTA$, pH=8; 10 mg/ml lysozyme; and 10.3% sucrose) were added. The solution was mixed and then incubated at 30° C. for 30–60 minutes, and then, about 18 ml of a solution that was 0.3M NaOH, 1% SDS, and prewarmed to 50° C. were added, mixed and the resulting mixture incubated at 60° C. for 5 minutes. The mixture was then cooled to room temperature, and 12 ml of a solution made by mixing 500 g phenol, 500 g $CHCl_3$, and 0.5 g 8-hydroxyquinoline in 200 ml $H_2O$ were added and mixed with the cell-extract. The phases were separated by centrifugation at 6000–8000 rpm for 10 minutes; approximately 45 ml of the resulting upper phase were transferred to a clean bottle.

Next, 4.5 ml of 3M sodium acetate (NaOAc) and 50 ml of isopropanol were added to the supernatant, and the solution was mixed and left at room temperature for 30 minutes. The solution was then centrifuged (8000 rpm for 30 minutes) and the resulting supernatant discarded. The pellet was resuspended in 7.5 ml TE buffer (10 mM Tris-HCl, pH=8, and 1 mM EDTA) containing 8 g of cesium chloride (CsCl). About 0.5 ml of a 10 mg/ml solution of ethidium bromide was added to the solution, which was then centrifuged at 40,000 rpm for 48 hours at 20° C. The fraction containing the plasmid band was extracted 3–5 times with isopropanol saturated with TE buffer and CsCl to remove the ethidium bromide. After the extractions, the sample was diluted with four volumes of TE buffer, and then, two-and-one-half volumes of ethanol were added. The resulting solution was mixed and incubated overnight at −20° C.

The precipitate resulting from the overnight incubation at −20° C. was collected by centrifugation (10,000 rpm for 30 minutes), dried, and reprecipitated twice. The precipitations were done by suspending the pellet in TE buffer, adding NaOAc to 0.3M, adding 2.5 volumes ethanol, chilling at −70° C. for 10–15 minutes, and then centrifuging the solution as above. The procedure yields about 100 μg of plasmid pSKC10 DNA, which were suspended in TE buffer at a concentration of 0.1 μg/μl and stored at 4° C.

EXAMPLE 2

Construction of Plasmids pSKCAA and pSKCBB

*Streptomyces lividans*/PIJ702 (ATCC 39155) is cultured and plasmid pIJ702 isolated in substantial accordance with the teachinbg of Example 1. Thiostrepton selection (10 μg/ml) is used to endure plasmid pIJ702 maintenance. The ~100 μg of plasmid pIJ702 DNA obtained are suspended in about 1 ml of TE and stored at 4° C.

About 700 ng (11 μl) of plasmid pIJ702 DNA are added to 4 μl of 10X BglII buffer (100 mM Tris-HCl, pH=7.4; 1.0M NaCl; 100 mM $MgCl_2$; 100 mM 2-mercaptoethanol; and 1 mg/ml bovine serum albumin (BSA)), 23 μl of $H_2O$, and 2 μl (~20 units; unit definitions herein correspond to those of New England Biolabs, 32 Tozer Road, Beverly, MA 01915-9990, unless otherwise indicated) of restriction enzyme BglII. The resulting reaction was incubated at 37° C. for one hour. The BglII-digested DNA is collected by adjusting the NaOAc concentration of the reaction mixture to 0.30M, adding two volumes of ethanol, chilling the reaction mixture to −70° C., and centrifuging to pellet the precipitated DNA. The pellet of BglII-digested plasmid pIJ702 DNA is resuspended in 100 μl of 50 mM Tris-HCl, pH=8.0. About 1 μl of a 1:100 dilution calf-intestinal alkaline phosphatase (Boehringer-Mannheim Biochemicals, 7941 Castleway Dr., P.O. Box 50816, Indianapolis, IN 46250) in 50 mM Tris-HCl, pH=8, is added to the solution of DNA, and the resulting reaction is incubated at 37° C. for 30 minutes. The reaction is terminated by incubating the reaction mixture at 70° C. for one hour.

About 10 μg of plasmid pSKC10 DNA in 100 μl of TE buffer were added to 20 μl of 10X BamHI buffer (1.5M NaCl; 60 mM Tris-HCl, pH=7.9; 60 mM $MgCl_2$; and 1 mg/ml BSA), 75 μl of $H_2O$, and 5 μl (~50 units) of restriction enzyme BamHI, and the resulting reaction was incubated at 37° C. for one hour. The BamHI-digested plasmid pSKC10 DNA was subjected to agarose gel electrophoresis, and the ~2.8 kb, tlrC-containing BamHI restriction fragment was isolated from the gel and prepared for ligation in substantial accordance with the restriction fragment isolation procedure described in Example 3, herein. About 2 μg of the desired fragment were obtained and suspended in 100 μl of TE buffer.

About 77 μl of the BglII-digested, alkaline phosphatase-treated plasmid pIJ702 DNA are added to 10 μl of the ~2.8 kb BamHI restriction fragment of plasmid pSKC10, 22 μl of $H_2O$, 11 μl of 3M NaOAc, and 300 μl of absolute ethanol. The solution is mixed, chilled at −70° C. for 30 minutes, and then centrifuged to pellet the DNA. The DNA is resuspended in 12 μl of 1X ligase buffer (50 mM Tris-HCl, pH=7.8; 10 mM $MgCl_2$; 20 mM dithiothreitol (DTT); 1.0 mM ATP; and 50 μg/ml BSA). About 1 μl (~1 unit, Boehringer-Mannheim) of T4 DNA ligase is added to the solution of DNA, and the resulting reaction is incubated at 15° C. overnight (~16 hours). The ligated DNA constitutes the desired plasmids pSKCAA and pSKCBB, which differ only with respect to the orientation of the ~2.8 kb BamHI restriction fragment. A restriction site and function map of plasmid pSKCAA is presented in FIG. 2 of the accompanying drawings. The ligated DNA is first used to transform *Streptomyces lividans* TK23 in accordance with the procedure of Example 8, , and about 1 μg of DNA is prepared from the *S. lividans* TK23/pSKCAA and *S. lividans* TK23/pSKCBB transformants to transform *Streptomyces fradiae* JS87 as described below.

The composition of the various solutions used in the transformation procedure is described in Example 8. *Streptomyces fradiae* JS87 can be isolated from *S. fradiae* JS87/pSKC10 in accordance with the procedure of Example 6. About 2 ml of a homogenized, sonicated culture of *S. fradiae* JS87 are inoculated into 20 ml of TSB, and the culture is incubated at 30° C. with aeration for about 16 hours. The culture is homogenized and sonicated, and about 2 ml are passaged into 20 ml of TSB with 0.3% w/v glycine. The culture is incubated at 29° C. with aeration for 16 hours. The culture is homogenized, sonicated, and re-passaged into 20 ml of TSB with 0.3% glycine as before. After the culture is incubated at 29° C. with aeration for 16 hours, the cells are collected, washed twice with about 5 ml of P media per wash, and resuspended in 20 ml of P media containing 1 mg/ml lysozyme. The cells are incubated at room temperature for 1.5 hours, washed twice with 5 ml of P media per wash, and resuspended in 2 ml of P media. The protoplasts are incubated on ice until use.

About 1 μg of transforming DNA in 20 μl of TE buffer is added to 50 μl of 1 mg/ml of the sodium salt of heparin in P media. The relatively large amount of DNA is necessary to overcome the endogenous restriction system of *S. fradiae* JS87. About 200 μl of protoplasts are added to the DNA/heparin solution and then mixed. About 0.9 ml of 55% polyethylene glycol (PEG) in P media is added to the DNA/protoplast solution and mixed. Varying aliquots of the mixture are added to 3 ml of R2 soft agar overlay and then plated onto R2 plates that had been dried at 37° C. for 3-4 days prior to use.

Tylosin-resistant transformants are selected by replica-plating regenerated protoplasts to AS1 medium containing 500 μg/ml of tylosin. Identification of tlrC-containing transformants can be facilitated by replicating the transformants to AS1 media containing low levels, ~2 μg/ml, of tylosin, incubating the plates at 29° C. for 7 days, and then replicating the colonies to AS1 plates containing 500 μg/ml of tylosin. Alternatively, tylosin-resistant transformants can be selected by overlaying the regenerating protoplasts with soft nutrient broth agar containing enough tylosin to give a final concentration of about 2 μg/ml. The regeneration plates are then incubated for 24 hours at 30° C. before the application of 2.5 ml per plate of SNA (at a temperature of 45°-50° C.) containing enough tylosin to give a final concentration of 500 μg/ml.

Selection for other antibiotic resistance-conferring determinants was performed as described in Example 8. Melanin production, or lack thereof, by transformants carrying plasmid pIJ702 derivatives was detected by incorporating tyrosine at 750 μg/ml into the regeneration media; those transformants possessing an intact tyrosinase gene become black after growth in the presence of tyrosine. Transformants are analyzed as described in Example 8. *S. fradiae* JS87/pIJ702 transformants are distinguished from *S. fradiae* JS87/pSKCAA and *S. fradiae* JS87/pSKCBB transformants by the color of the colonies on the transformation plates and by the fact that plasmid pIJ702 does not confer tylosin resistance. Plasmid pIJ702 carries an intact tyrosinase gene; thus *S. fradiae* JS87/pIJ702 transformants are black on tyrosine-containing plates. The tyrosinase gene is inactivated during the construction of plasmids pSKCAA and pSKCBB; consequently, *S. fradiae* JS87/pSKCAA transformants are not black on tyrosine-containing plates.

EXAMPLE 3

Construction of Plasmids pSKC11 and pSKC12

A. Construction of Plasmid pHJL289

Plasmid pHJL284 comprises the tylF gene and is disclosed and claimed in U.S. patent application No. 07/018,237, filed Feb. 24, 1987, is a continuation-in-part of U.S. patent application No. 890,670, filed July 25, 1986, now abandoned, which is a continuation-in-part of U.S. patent application Ser. No. 842,330, filed Mar. 21, 1986, now abandoned, incorporated herein by reference. Plasmid DNA was obtained from *E. coli* K12 HB101/pHJL284 (NRRL B-18044) to use in the construction of plasmids pSKC11 and pSKC12 in accordance with the following procedure, which is adapted from Maniatis et al., 1982, *Molecular Cloning* (Cold Spring Harbor Laboratory). This same procedure was used, but on a smaller scale and with the ultracentrifugation steps replaced with phenol followed by chloroform extractions, to prepare the plasmid DNA used to identify the various *E. coli* transformants of the present invention.

The lyophilized *E. coli* K12 HB101/pHJL284 cells obtained under the accession number NRRL B-18044 are plated on L-agar (L broth with 15 g of agar per liter) plates containing 100 μg/ml ampicillin to obtain single-colony isolates, one of which is used to inoculate 500 ml of L broth (10 g of Bacto-tryptone, 10 g of NaCl, and 5 g of Bacto-Yeast extract per liter) containing 100 μg/ml ampicillin. The culture is incubated at 37° C. with aeration until the cells reach stationary phase.

About 500 ml of stationary-phase *E. coli* K12 JM109/pHJL284 cells are harvested by centrifugation at 4000Xg for 10 minutes at 4° C., and the supernatant is discarded. The cell pellet is washed in 100 ml of ice-cold STE buffer (0.1M NaCl; 10 mM Tris-HCl, pH 7.8; and 1 mM EDTA). After the cell pellet is washed, the pellet is resuspended in 10 ml of Solution 1 (50 mM glucose; 25 mM Tris-HCl, pH=8.0; and 10 mM EDTA) that contains 5 mg/ml lysozyme. The mixture is incubated at room temperature for 10 minutes. Twenty ml of Solution 2 (0.2N NaOH and 1% SDS) are then added to the lysozyme-treated cells, and the solution is gently mixed by inversion. The mixture is incubated on ice for 10 minutes.

Fifteen ml of ice-cold, 5M potassium acetate, pH=4.8, are added to the lysed-cell mixture, and the solution is mixed by inversion. The solution is incubated on ice for 10 minutes. The 5M potassium acetate solution is prepared by adding 11.5 ml of glacial acetic acid to 28.5 ml of water and 60 ml of 5M potassium acetate; the resulting solution is 3M with respect to potassium and 5M with respect to acetate.

The lysed cell mixture is centrifuged in a Beckman SW27 rotor (or its equivalent) at 20,000 rpm for 20 minutes at 4° C. The cell DNA and debris forms a pellet on the bottom of the tube. About 36 ml of supernatant are recovered, and 0.6 volumes of isopropanol are added, mixed, and the resulting solution left at room temperature for 15 minutes. The plasmid DNA is collected by centrifugation at 12,000Xg for 30 minutes at room temperature. The supernatant is discarded, and the DNA pellet is washed with 70% ethanol at room temperature. The ethanol wash is decanted, and the pellet is dried in a vacuum desiccator. The pellet is then resuspended in 8 ml of TE buffer.

Eight grams of CsCl are added to the DNA solution. About 0.8 ml of a 10 mg/ml solution of ethidium bromide in water are added for each 10 ml of CsCl-DNA solution. The final density of the solution is about 1.55 g/ml. The solution is transferred to a Beckman Type 50 centrifuge tube, filled to the top with paraffin oil, sealed, and centrifuged at 45,000 rpm for 24 hours at 20° C. After centrifugation, two bands of DNA are visible in ordinary light. The cap is removed from the tube, and the lower DNA band is recovered using a syringe with a #21 hypodermic needle inserted through the side of the centrifuge tube.

The ethidium bromide is removed from the solution of plasmid DNA by several extractions with water-saturated 1-butanol, and the CsCl is removed by dialysis against TE buffer. After extractions with buffered phenol and then chloroform, the DNA is precipitated, washed with 70% ethanol, and dried. About 1 mg of plasmid pHJL284 DNA was obtained and dissolved in 10 ml of TE buffer.

About 10 μg of plasmid pHJL284 in 10 μl of TE buffer were added to 4 μl of 10X BamHI buffer, 14 μl of H$_2$O and 2 μl (~20 units) of restriction enzyme BamHI. The resulting reaction was incubated at 37° C. for 2 hours. The BamHI-digested plasmid pHJL284 DNA was precipitated with NaOAc and ethanol and resuspended in 20 μl of 1X EcoRI buffer (100 mM Tris-HCl, pH=7.5; 50 mM NaCl; 5 mM MgCl$_2$; and 100 μg/ml BSA) that contained 1 μl (~20 units) of restriction enzyme EcoRI. The reaction mixture was incubated at 37° C. for 2 hours. The BamHI-EcoRI-digested plasmid pHJL284 DNA was then electrophoresed on a 1% agarose gel until the desired ~2.2 kb, tylF-containing BamHI-EcoRI restriction fragment was clearly separated from the other digestion products. Visualization of the electrophoresed DNA was accomplished by staining the gel in a dilute solution (0.5 μg/ml) of ethidium bromide and exposing the stained gel to long-wave UV light.

After the desired fragment was located, a small slit was made in the gel in front of the fragment, and a small piece of Schleicher and Schuell (Keene, NH 03431) NA-45 DEAE membrane was placed in the slit. Upon further electrophoresis, the ~2.2 kb BamHI-EcoRI restriction fragment was non-covalently bound to the DEAE membrane. After the desired fragment was bound to the DEAE membrane, the membrane was removed and rinsed with low salt buffer (100 mM KCl; 0.1 mM EDTA; and 20 mM Tris-HCl, pH=8). Next, the membrane was placed in a small tube and immersed in high salt buffer (1M NaCl; 0.1 mM EDTA; and 20 mM Tris-HCl, pH=8) and then incubated at 65° C. for one hour to remove the DNA from the DEAE paper. After the 65° C. incubation, the incubation buffer was collected and the membrane rinsed with high salt buffer. The rinse solution was pooled with the incubation buffer before collecting the desired DNA fragments.

The volume of the high salt-DNA solution was adjusted so that the NaOAc concentration was 0.30M, and then three volumes of cold, absolute ethanol were added. The resulting solution was mixed and placed at −70° C. for 10–20 minutes. The solution was centrifuged at 15,000 rpm for 15 minutes. After a precipitation with ethanol and NaOAc to remove residual salt, the DNA pellet was rinsed with 70% ethanol, dried, resuspended in 10 μl of TE buffer, and constituted ~1.0 μg of the desired ~2.2 kb BamHI-EcoRI restriction fragment of plasmid pHJL284.

Plasmid pHJL401 is a Streptomyces cloning vector disclosed and claimed in U.S. patent application Ser. No. 841,920, filed Mar. 20, 1986, incorporated herein by reference. The construction protocol for plasmid pHJL401 is described in Example 14 of Ser. No. 841,920. About 1 μg of plasmid pHJL401 DNA in one μl of TE buffer was added to 1 μl of 10X BamHI buffer, 1 μl (~10 units) of restriction enzyme BamHI, and 7 μl of H$_2$O. The resulting reaction was incubated at 37° C. for about 2 hours. The BamHI-digested plasmid pHJL401 DNA was precipitated with NaOAc and ethanol and resuspended in 20 μl of 1X EcoRI buffer that contained 1 μl (~20 units) of restriction enzyme EcoRI. The resulting reaction was incubated at 37° C. for 2 hours. Then, 100 μl of 50 mM Tris-HCl, pH=8 were added to the solution of BamHI-EcoRI-digested plasmid pHJL401 DNA together with 1 μl of a 1:100 dilution of calf-intestinal alkaline phosphatase (Boehringer-Mannheim Biochemicals), and the reaction mixture was again placed at 37° C. for 30 minutes.

About 34 μl of the BamHI-digested, phosphatase-treated plasmid pHJL401 DNA were added to 1 μl of the solution of the ~2.2 kb EcoRI-BamHI restriction fragment of plasmid pHJL284. The mixture of DNA was precipitated with NaOAc and ethanol as described above, and the pellet was resuspended in 10 μl of 1X ligase buffer containing 6 units of T4 DNA ligase (Boehringer-Mannheim). The ligation reaction was incubated at 4° C. overnight (~16 hours) and constituted the desired plasmid pHJL289. A restriction site and function map of plasmid pHJL289 is presented in FIG. 3 of the accompanying drawings. The ligated DNA was used to transform *E. coli* K12 JM109 in substantial accordance with the procedure described below.

To prepare *E. coli* K12 JM109 cells that are competent for transformation, the lyophils of *E. coli* K12 JM109 obtained from the ATCC under the accession number ATCC 53323 are reconstituted to isolate single colonies. One single-colony isolate of JM109 is inoculated into 5 ml of L broth that contains 10 mM MgSO$_4$ and 10 mM MgCl$_2$, and the culture is incubated at 37° C. overnight with aeration. Fifty μl of the overnight culture were used to inoculate 5 ml of L broth that contained 10 mM MgSO$_4$ and 10 mM MgCl$_2$. The culture was incubated at 37° C. overnight with aeration. The following morning, the culture was diluted to 200 ml with L broth that contained 10 mM MgSO$_4$ and 10 mM MgCl$_2$. The diluted culture was incubated at 37° C. with aeration until the absorbance at 550 nm (A$_{550}$) was about 0.5, which indicated a cell density of about $1 \times 10^8$ cells/ml. The culture was cooled for ten minutes in an ice-water bath, and the cells were then collected by centrifugation at 4000Xg for 10 minutes at 4° C. The cell pellet was resuspended in 100 ml of cold 10 mM NaCl and then immediately repelleted by centrifugation. The cell pellet was resuspended in 100 ml of 30 mM CaCl$_2$ and incubated on ice for 20 minutes.

The cells were again collected by centrifugation and resuspended in 10 ml of 30 mM CaCl$_2$. A one-half ml aliquot of the cells was added to the ligated DNA prepared above; the DNA had been made 30 mM in CaCl$_2$. The cell-DNA mixture was incubated on ice for one hour, heat-shocked at 42° C. for 90 seconds, and then chilled on ice for about two minutes. The cell-DNA mixture was diluted into 10 ml of L broth in a 125 ml flask and incubated at 37° C. for one hour.

The EcoRI and BamHI sites on plasmid pHJL401 reside within a polylinker that itself forms part of the DNA sequence encoding the lacZ α-fragment. Expression of the lacZ α-fragment in an *E. coli* ΔM15, or similar type, mutant, such as JM109, restores the mutant's ability to produce a functional β-galactosidase enzyme. Thus, plasmid pHJL401 can restore β-galactosidase activity to an *E. coli* ΔM15 mutant. However, insertion of DNA into a restriction site of the polylinker on plasmid pHJL401, as occurs in the construction of plasmid pHJL289, disrupts the lacZ α-fragment coding sequence and concomitantly destroys the ability of the pHJL 401 derivative to complement a ΔM15-type mutation. β-galactosidase can hydrolyze X-Gal, which is 5-bromo-4-chloro-3-indolyl-β-D-galactopyranoside, a colorless compound, to an indigo-colored product and thus allows for a convenient screening method for discriminating between transformants containing starting plasmid pHJL401 or modified plasmid, such as plasmid pHJL289.

Thus, aliquots of the transformation mixture were plated on L-agar plates containing 100 μg ampicillin/ml, 40 μg X-gal/ml, and 40 μg IPTG/ml. IPTG, isopropyl β-D-thiogalactopyranoside, serves to induce the lac promoter present on plasmid pHJL401. The plates were incubated at 37° C. overnight. Colonies that contain a plasmid with an insert, such as *E. coli* K12 JM109/pHJL289, are white, whereas *E. coli* K12 JM109/pHJL401 transformants are indigo-colored on these plates. Several ampicillin-resistant, white colonies were selected and then screened by restriction analysis of their plasmid DNA for the presence of the ~2.2 kb BamHI-EcoRI restriction fragment that cnntains tylF. In this manner, the desired *E. coli* K12 JM109/pHJL289 transformants were identified and isolated. Plasmid pHJL289 DNA was obtained for use in subsequent constructions in substantial accordance with the plasmid isolation procedure described for plasmid pHJL401.

B. Construction of Plasmids pSKC11 and pSKC12

Plasmid pHJL289 was digested with restriction enzyme BamHI, treated with alkaline phosphatase, and ligated to the ~2.8 kb, tlrC-containing BamHI restriction fragment of plasmid pSKC10 in substantial accordance with the procedure of Example 2. The ligated DNA constituted the desired plasmids pSKC11 and pSKC12, which differ only with respect to the orientation of the ~2.8 kb, tlrC-containing restriction fragment. The ligated DNA was used to transform *E. coli* K12 JM109 in substantial accordance with the procedure described above. However, no X-Gal or IPTG was added to the transformation plates. Plasmid DNA was obtained from the transformants in substantial accordance with the procedure described in Example 3A and was used to transform *Streptomyces fradiae* JS87 in substantial accordance with the procedure of Example 2. A restriction site and function map of plasmid pSKC11 is presented in FIG. 4 of the accompanying drawings.

EXAMPLE 4

Construction of Plasmids pSVB49 and pSVB50

Plasmid pIJ903 (JICC 3417) is digested with restriction enzyme BamHI, treated with alkaline phosphatase, and ligated to the ~2.8 kb tlrC-containing BamHI restriction fragment of plasmid pSKC10 in substantial accordance with the procedure of Example 2. The ligated DNA constitutes the desired plasmids pSVB49 and pSVB50, which differ only with respect to the orientation of the ~2.8 kb, tlrC-containing restriction fragment. The ligated DNA is used to transform *E. coli*, and after confirmation of structure, independent preparations of plasmids pSVB49 and pSVB50 are used to transform Streptomyces fradiae JS87 in substantial accordance with the procedure described in Example 2. A restriction site and function map of plasmid pSVB49 is presented in FIG. 5 of the accompanying drawings. Plasmid pIJ903 contains the β-lactamase gene of plasmid pBR327; therefore, the *E. coli* transformants of plasmids pSVB49 and pSVB50 are selected on the basis of their ampicillin-resistant phenotype.

EXAMPLE 5

Construction of Plasmids pSKCEE, pSKCFF, pSVB34, pSVB48, and pSVB57

A. Construction of Plasmids pSKCEE and pSKCFF

Plasmid pIJ941 (JICC 3338) is digested with restriction enzyme BamHI, treated with alkaline phosphatase, and ligated to the ~2.8 kb tlrC-containing BamHI restriction fragment of plasmid pSKC10 in substantial accordance with the procedure of Example 2. The ligated DNA constitutes the desired plasmids pSKCEE and pSKCFF, which differ only with respect to the orientation of the ~2.8 kb, tlrC-containing restriction fragment. The ligated DNA is used to transform *Streptomyces fradiae* JS87 in substantial accordance with the procedure of Example 2. A restriction site and function map of plasmid pSKCEE is presented in FIG. 6 of the accompanying drawings.

B. Construction of Plasmid pSVB34

Figure 7:
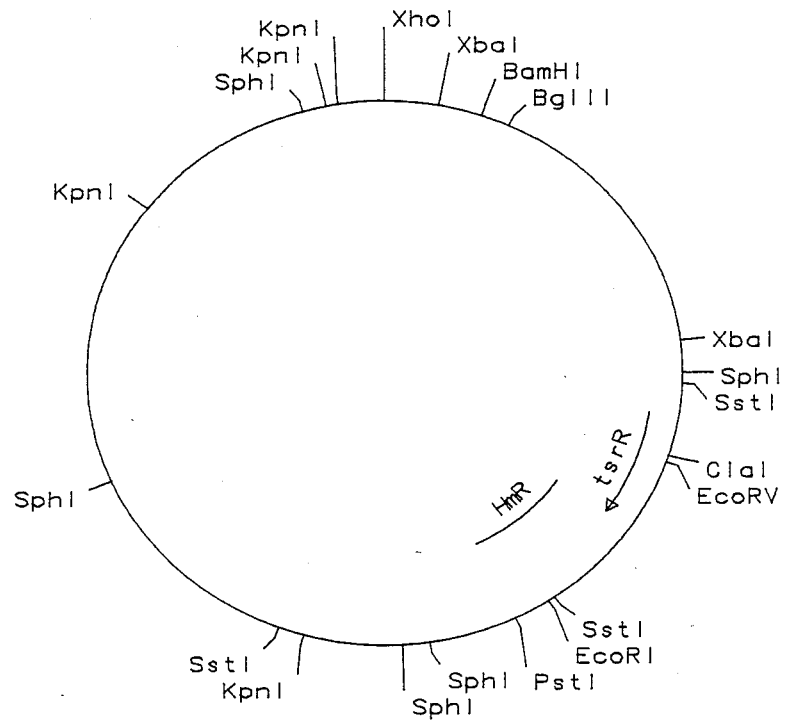
FIG. 7 is a restriction site and function map of plasmid pIJ941.
Figure 8:
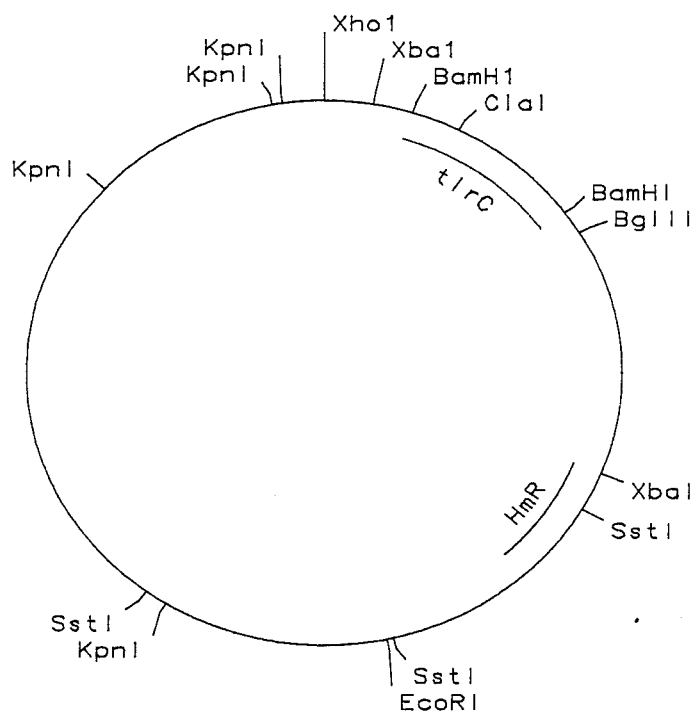
FIG. 8 is a restriction site and function map of plasmid pSVB48.

A restriction site and function map of plasmid pIJ941 is presented in FIG. 7 of the accompanying drawings. About 5 μg of plasmid pIJ941 in 50 μl of TE buffer were dissolved in 10 μl of 10X ClaI buffer (0.5M NaCl; 60 mM Tris-HCl, pH=7.9; 60 mM MgCl$_2$; and 1 mg/ml BSA) and 85 μl of H$_2$O. About 5 μl (~25 units) of restriction enzyme ClaI were added to the solution of plasmid pIJ941 DNA, and the resulting reaction was incubated at 37° C. for 2 hours. The ClaI-digested plasmid pIJ941 DNA was precipitated with NaOAc and ethanol and resuspended in 20 μl of 1X EcoRV buffer that contained 1 μl (~20 units) of restriction enzyme EcoRV. The resulting reaction was incubated at 37° C. for 2 hours. The EcoRV-ClaI-digested plasmid pIJ941 DNA was precipitated with ethanol and NaOAc and resuspended in 50 μl of 1X Klenow buffer (40 mM KPO$_4$, pH=7.5; 6.6 mM MgCl$_2$; 1.0 mM 2-mercaptoethanol; 33 μM dATP; 33 μM TTP; 33 μM dGTP; and 33 μM dCTP) that contained 1 μl (~5 units) of Klenow enzyme, the large fragment of subtilisin-treated, *E. coli* DNA polymerase I. The resulting reaction was incubated at 37° C. for 30 minutes; then, the DNA was precipitated with ethanol and NaOAc.

The EcoRV-ClaI-digested, Klenow-treated plasmid pIJ941 DNA was resuspended in 10 μl of 1X ligase buffer containing 1 μl (Boehringer-Mannheim Biochemicals) of T4 DNA ligase, and the resulting reaction was incubated at 4° C. overnight. The ligated DNA constituted the desired plasmid pSVB34 and was used to transform *Streptomyces lividans* TK23 in substantial accordance with the proceduure of Example 8. The desired *S. lividans* TK23/pSVB34 transformants were identified by their hygromycin-resistant, thiostrepton-sensitive phenotype; S. lividans TK23/pIJ941 cells are resistant to both hygromycin and thiostrepton. Hygromycin is added to the transformation plates to select for hygromycin-resistant transformants at a concentration of 200 µg/ml.

C. Final Construction of Plasmids pSVB48 and pSVB57

Plasmid pSVB34 DNA was prepared in substantial accordance with the procedure of Example 1, except selection was for hygromycin resistance (200 µg/ml) rather than thiostrepton resistance. Plasmid pSVB34 is digested with restriction enzyme BamHI, treated with alkaline phosphatase, and ligated to the ~2.8 kb tlrC-containing BamHI restriction fragment of plasmid pSKC10 in substantial accordance with the procedure of Example 2. The ligated DNA constitutes the desired plasmids pSVB48 and pSVB57, which differ only with respect to the orientation of the ~2.8 kb, tlrC-containing restriction fragment. The ligated DNA is used to transform Streptomyces fradiae JS87 in substantial accordance with the procedure described in Example 2. A restriction site and function map of plasmid pSVB48 is presented in FIG. 8 of the accompanying drawings.

EXAMPLE 6

Isolation of Streptomyces fradiae JS87 from S. fradiae JS87/pSKC10 (NRRL 18072)

Plasmid pSKC10 carries determinants for thiostrepton resistance and tylosin resistance and will segregate in the absence of selection. To isolate Streptomyces fradiae JS87 from S. fradiae JS87/pSKC10 about 20 ml of trypticase-soya broth (TSB) are inoculated with 2 ml of preserved culture or with a colony from a plate (which should be homogenized in TSB prior to inoculation). The culture is incubated for 24-48 hours at 29° C. The culture is homogenized and sonicated, and 2 ml of the culture are again inoculated into 20 ml TSB, and the growth cycle is repeated. The culture is again homogenized and sonicated and then diluted in TSB and plated on AS1 medium supplemented with 10 mM MgCl$_2$ to obtain single-colony isolates. The plates are incubated at 29° C. for 7-14 days until colonies have grown and sporulated. The plates with well-spaced colonies are replicated to plates containing AS1 and MgCl$_2$ and to plates containing AS1, MgCl$_2$, and 25 µg/ml of thiostrepton. The replica plates are incubated at 29° C. for 7-14 days. Colonies that are tylosin-sensitive and able to grow only on plates that contain no thiostrepton are Streptomyces fradiae JS87 and can be used in the transformation procedure described in Example 8.

EXAMPLE 7

Construction of Plasmids pSVB51, pSVB52, pSVB53 and pSVB54

A. Construction of Plasmid pSVB25

Streptomyces lividans/pIJ702 (ATCC 39155) was cultured and plasmid pIJ702 isolated in substantial accordance with the teaching of Example 1. Thiostrepton selection (10 µg/ml) was used to ensure plasmid pIJ702 maintenance. The ~100 µg of plasmid pIJ702 DNA obtained were suspended in 1 ml of TE and stored at 4° C.

About 500 ng (5 µl) of plasmid pIJ702 DNA were added to 2 µl of 10X SacI buffer (60 mM Tris-HCl, pH=7.4; 60 mM MgCl$_2$; 60 mM 2-mercaptoethanol; and 1 mg/ml bovine serum albumin (BSA)), 12 µl of H$_2$O, and 1.5 µl (~15 units) of restriction enzyme SacI, an isoschizomer of restriction enzyme SstI. The resulting reaction was incubated at 37° C. for one hour, when about 3 µl of the reaction mixture were removed and subjected to agarose gel electrophoresis to determine completeness of digestion. About 4 µl of 10X BglII buffer, 16 µl of H$_2$O, and 2 µl (~16 units) of restriction enzyme BglII were added to the solution of SacI-digested plasmid pIJ702 DNA, and the resulting reaction was incubated at 37° C. for 1 hour. About 6 µl of the reaction mixture were removed to check completeness of digestion.

The SacI-BglII-digested plasmid pIJ702 DNA was collected by adjusting the NaOAc concentration of the reaction mixture to 0.30M, adding two volumes of ethanol, chilling the reaction mixture to −70° C., and centrifuging to pellet the precipitated DNA. The pellet of BglII-SacI-digested plasmid pIJ702 DNA was resuspended in 100 µl of 50 mM Tris-HCl, pH=8.0. About 1 µl of a 1:100 dilution calf-intestinal alkaline phosphatase (Boehringer-Mannheim) in 50 mM Tris-HCl, pH=8, was added to the solution of DNA, and the resulting reaction was incubated at 37° C. for 30 minutes. The reaction was terminated by incubating the reaction mixture at 70° C. for one hour.

Plasmid pSVB9 was isolated from Streptomyces lividans TK23/pSVB9 (NRRL 18073) in substantial accordance with the procedure of Example 1. A restriction site and function map of plasmid pSVB9 is presented in FIG. 10 of the accompanying drawings. About 625 ng of plasmid pSVB9 DNA in 25 µl of TE buffer were added to 6 µl of 10X SacI buffer, 26 µl of H$_2$O, and 2 µl (~20 units) of restriction enzyme SacI, and the resulting reaction was incubated at 37° C. for one hour. About 3 µl of 1M NaCl and 2 µl (~20 units) of restriction enzyme ClaI were then added to the reaction mixture, which was incubated at 37° C. for another hour. The ClaI-digestion lowers the frequency of undesired ligation products during the ligation to construct plasmid pSVB25. About 8 µl of the reaction mixture were subjected to agarose gel electrophoresis to check completeness of the digestions, and 1 µl of 1M NaCl and 1 µl (~8 units) of restriction enzyme BglII were added to the remaining solution of ClaI-SacI-digested DNA; the reaction mixture was incubated for another hour at 37° C. About 8 µl of the reaction mixture were removed and electrophoresed to check the completeness of the BglII digestion.

Figure 11:
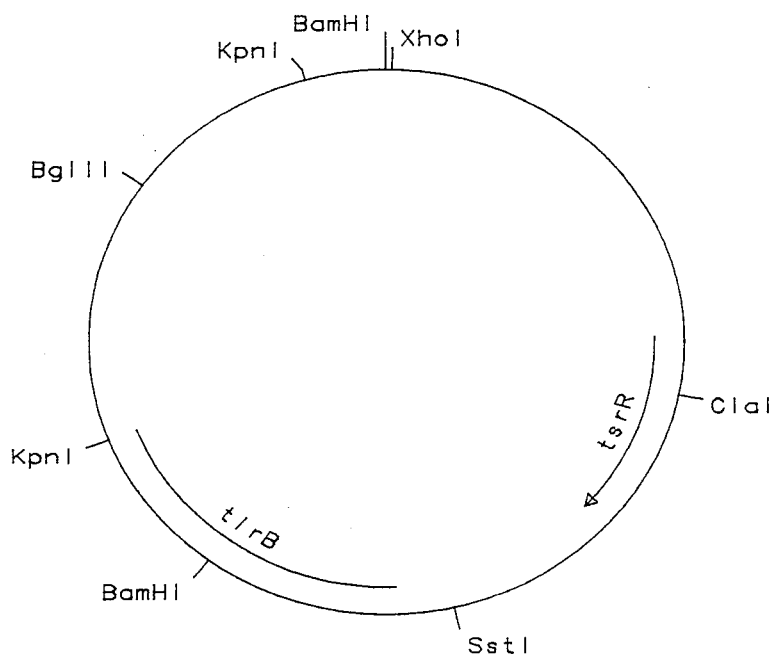
FIG. 11 is a restriction site and function map of plasmid pSVB25.

About 77 µl of the BglII-SacI-digested, alkaline phosphatase-treated plasmid pIJ702 DNA were added to 32 µl of the BglII-SacI-ClaI-digested plasmid pSVB9 DNA, 11 µl of 3M NaOAc, and 300 µl of absolute ethanol. The solution was mixed, chilled at −70° C. for 30 minutes, and then centrifuged to pellet the DNA. The DNA was resuspended in 12 µl of 1X ligase buffer. About 1 µl (~1 unit, Boehringer-Mannheim) of T4 DNA ligase was added to the solution of DNA, and the resulting reaction was incubated at 15° C. overnight (~16 hours). The ligated DNA constituted the desired plasmid pSVB25 DNA. A restriction site and function map of plasmid pSVB25 is presented in FIG. 11 of the accompanying drawings. The ligated DNA was used to transform Streptomyces lividans TK23 in substantial accordance with the procedure described in Example 8, below.

*Streptomyces lividans* TK23/pIJ702 transformants were distinguished from *S. lividans* TK23/pSVB25 transformants by the color of the colonies on the transformation plates. Plasmid pIJ702 carries an intact tyrosinase gene; thus *S. lividans* TK23/pIJ702 transformants are black on tyrosine-containing plates. The tyrosinase gene is inactivated during the construction of plasmid pSVB25; consequently, *S. lividans* TK23/pSVB25 transformants are not black on tyrosine-containing plates. Plasmid pSVB25 was isolated from the transformants for use in subsequent constructions in substantial accordance with the procedure of Example 1.

B. Construction of Plasmids pSVB36 and pSVB37

*Streptomyces lividans* TK/23/pSVB2 (NRRL 15880) was cultured and treated in substantial accordance with the procedure of Example 1 to isolate plasmid pSVB2 DNA. A restriction site and function map of plasmid pSVB2 is presented in FIG. 9 of the accompanying drawings. About 500 ng of plasmid pSVB2 DNA in 5 μl of TE buffer were added to 12 μl of H$_2$O, 2 μl of 10X ClaI buffer (0.5M NaCl; 60 mM Tris-HCl, pH=7.9; 60 mM MgCl$_2$; and 1 mg/ml BSA), and 2 μl (~14 units) of restriction enzyme ClaI, and the resulting reaction was incubated at 37° for one hour. The ClaI digestion reduces undesired ligation products in the ligation to produce plasmids pSVB36 and pSVB37.

About 1 μl of 1M NaCl and 1 μl (~8 units) of restriction enzyme BglII were added to the solution of ClaI-digested plasmid pSVB2 DNA, and the reaction was incubated at 37° C. for another hour. About 5 μl of the reaction mixture were removed and subjected to agarose gel electrophoresis to determine completeness of digestion. About 4 μl of 10X BamHI buffer, 19 μl of H$_2$O, and 2 μl (~48 units) of restriction enzyme BamHI were added to the remaining ~17 μl of BglII-ClaI-digested plasmid pSVB2 DNA, and the reaction mixture was incubated at 37° C. for one hour.

About 500 ng of plasmid pSVB25 DNA (prepared from *Streptomyces lividans* TK23/pSVB25 cells in substantial accordance with the procedure described in Example 1, above) in 5 μl of TE buffer were added to 11 μl of H$_2$O, 2 μl of 10X BglII buffer, and 2 μl (~16 units) of restriction enzyme BglII, and the resulting reaction was incubated at 37° C. for one hour. About 5 μl of the reaction mixture were subjected to agarose gel electrophoresis to determine the completeness of the BglII digestion, and the remaining BglII-digested plasmid pSVB25 DNA was precipitated with ethanol and treated with calf-intestinal alkaline phosphatase in substantial accordance with the procedure of Example 2.

Figure 12:
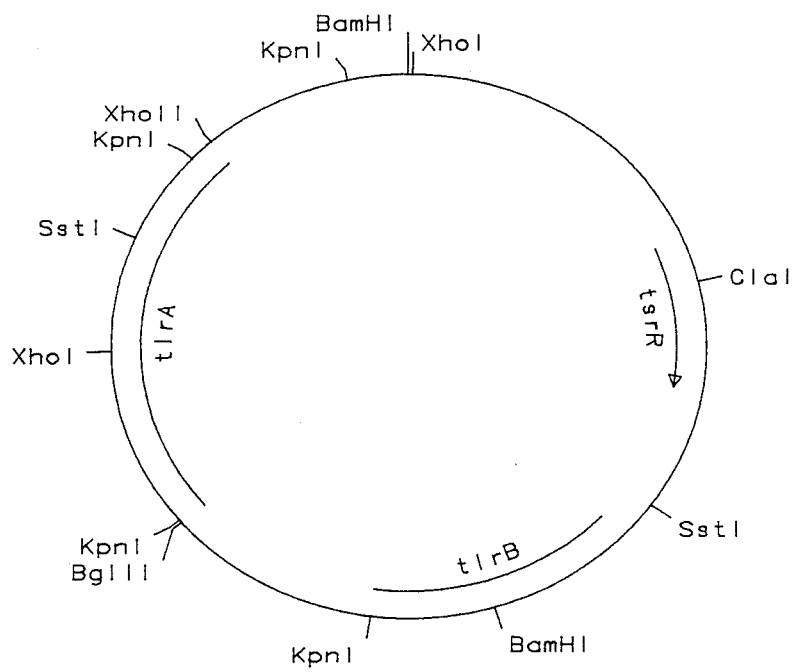
FIG. 12 is a restriction site and function map of plasmid pSVB36.

About 25 μl of the ClaI-BglII-BamHi-digested plasmid pSVB2 DNA and about 67 μl of the BglII-digested, alkaline phosphatase-treated plasmid pSVB25 DNA were mixed together with 9.2 μl of 3M NaOAc and 250 μl of ethanol. The mixture was chilled at −70° C. for 30 minutes and then centrifuged to pellet the DNA. The pellet was resuspended in 10 μl of 1X ligase buffer that contained 1 unit of T4 DNA ligase, and the resulting reaction was incubated at 15° C. overnight. The ligated DNA constituted the desired plasmids pSVB36 and pSVB37, which differ only with respect to the orientation of the ~2.9 kb, tlrA-containing restriction fragment. Restriction site and function maps of plasmids pSVB36 and pSVB37 are respectively presented in FIGS. 12 and 14 of the accompanying drawings. About 5 μl of the ligated DNA were used to transform *Streptomyces lividans* TK23 in substantial accordance with the procedure described in Example 8. The desired *S. lividans* TK23/pSVB36 and *S. lividans* TK23/pSVB37 transformants were identified by their tylosin-resistant phenotype and by restriction enzyme analysis of their plasmid DNA. Plasmid pSVB36 and pSVB37 DNA was isolated from the transformants for use in subsequent constructions in substantial accordance with the procedure of Example 1.

C. Construction of Plasmids pSVB51, pSVB52, pSVB53, and pSVB54

Plasmid pSVB36 is digested with restriction enzyme BglII, treated with alkaline phosphatase, and ligated to the ~2.8 kb, tlrC-containing BamHI restriction fragment of plasmid pSKC10 in substantial accordance with the procedure of Example 2, except that the digestion is with restriction enzyme BglII in 1X BglII reaction buffer. The ligated DNA constitutes the desired plasmids pSVB51 and pSVB52, which differ only with respect to the orientation of the ~2.8 kb, tlrC-containing restriction fragment. A restriction site and function map of plasmid pSVB51 is presented in FIG. 13 of the accompanying drawings. The ligated DNA is used to transform *Streptomyces fradiae* JS87 in substantial accordance with the procedure of Example 2.

Plasmid pSVB37 is likewise digested with restriction enzyme BglII, treated with alkaline phosphatase, and ligated to the ~2.8 kb, tlrC-containing BamHI restriction fragment of plasmid pSKC10 to yield plasmids pSKC53 and pSKC54, which differ only with respect to the orientation of the ~2.8 kb, tlrC-containing restriction fragment. A restriction site and function map of plasmid pSVB53 is presented in FIG. 15 of the accompanying drawings. The ligated DNA is used to transform *Streptomyces fradiae* JS87 in substantial accordance with the procedure of Example 2.

EXAMPLE 8

Construction of *Streptomyces lividans* TK23 Transformants

A. List of Solutions

The following solutions are referred to throughout the Examples and are presented here for clarity.

| 1. P medium (~100 ml): | |
|---|---|
| Ingredient | Amount |
| Sucrose | 10.3 g |
| K$_2$SO$_4$ | 0.025 g |
| Trace element solution (see #3) | 0.2 ml |
| MgCl$_2$.6H$_2$O | 0.203 g |
| Water | 80 ml |
| After autoclaving add: | |
| KH$_2$PO$_4$ (0.5%) | 1 ml |
| CaCl$_2$.2H$_2$O (3.68%) | 10 ml |
| (N—tris-(hydroxymethyl)-methyl-2-aminoethane sulphonic acid), "TES" buffer, 0.25 M, pH = 7.2 | 10 ml |

| 2. L medium (~100 ml): | |
|---|---|
| Ingredient | Amount |
| Sucrose (10.3%) | 100 ml |
| TES buffer, pH 7.2 (0.25 M) | 10 ml |
| K$_2$SO$_4$ (2.5%) | 1 ml |
| Trace element solution (see #3) | 0.2 ml |
| KH$_2$PO$_4$ (0.5%) | 1 ml |

-continued

| | |
|---|---|
| MgCl$_2$ (2.5 M) | 0.1 ml |
| CaCl$_2$ (0.25 M) | 1 ml |
| Lysozyme | 1 mg/ml |
| The L medium is filter sterilized after preparation. | |

3. Trace element solution (~1 l):

| Ingredient | Amount |
|---|---|
| ZnCl$_2$ | 40 mg |
| FeCl$_3$.6H$_2$O | 200 mg |
| CuCl$_2$.2H$_2$O | 10 mg |
| MnCl$_2$.4H$_2$O | 10 mg |
| Na$_2$B$_4$O$_7$.10H$_2$O | 10 mg |
| (NH$_4$)$_6$Mo$_7$O$_{24}$.4H$_2$O | 10 mg |
| H$_2$O | 1 l |

4. R2 Regeneration Medium (~1 l):

| Ingredient | Amount |
|---|---|
| Sucrose | 103 g |
| K$_2$SO$_4$ | 0.25 g |
| Trace element solution | 2 ml |
| MgCl$_2$.6H$_2$O | 10.12 g |
| glucose | 10 g |
| L-asparagine.1H$_2$O | 2.0 g |
| casamino acids | 0.1 g |
| Agar | 22 g |
| Water | to 700 ml |
| After autoclaving add: | |
| KH$_2$PO$_4$ (0.05 g/100 ml) | 100 ml |
| CaCl$_2$ (2.22 g/100 ml) | 100 ml |
| TES Buffer (5.73 g/100 ml, pH = 7.2) | 100 ml |
| NaOH (5 N) | 1 ml |

5. T medium (~14.5 ml):

| Ingredient | Amount |
|---|---|
| Sucrose (10.3%) | 2.5 ml |
| Distilled water | 7.5 ml |
| Trace element solution | 20 μl |
| K$_2$SO$_4$ (2.5%) | 100 μl |
| CaCl$_2$ (5 M) | 217 μl |
| Tris-maleic acid, pH = 8 (1 M) | 543 μl |
| Polyethylene glycol 1000 | 3.63 g |

All components were sterilized before use. The liquid components were mixed and then added to the appropriate amount of molten polyethylene glycol. The first four ingredients may be pre-mixed and stored at room temperature for at least one month.

6. Soft nutrient agar (SNA, ~1 l):

| Ingredient | Amount |
|---|---|
| Difco Bacto Nutrient Broth | 8 g |
| Agar | 5 g |

7. R2YE medium is R2 medium with 20 ml of 25% yeast extract added per liter.

8. Yeast Extract — Malt Extract (YEME, ~1 l):

| Ingredient | Amount |
|---|---|
| Yeast extract | 3 g |
| Peptone | 5 g |
| Malt extract | 3 g |
| Glucose | 10 g |

9. YEME + 34% Sucrose Liquid Complete Medium is YEME with 340 g/liter of sucrose.

10. YMX Media (~1 l):

| Ingredient | Amount |
|---|---|
| Yeast extract | 3 g |
| Malt extract | 3 g |
| Glucose | 2 g |
| Agar | 20 g |

11. AS1 Media:

| Ingredient | Amount |
|---|---|
| Yeast Extract | 1.0 |

-continued

| | |
|---|---|
| L-Alanine | 0.2 g |
| L-Arginine (free base) | 0.2 g |
| L-Asparagine | 0.5 g |
| Soluble Starch | 5.0 g |
| NaCl | 2.5 g |
| Na$_2$SO$_4$ | 10.0 g |
| Meer Agar | 20.0 g |

Deionized water is added to bring the final volume to one liter. The pH is adjusted to pH=7.5, and the solution is sterilized (25 minutes @ 121° C.) before use.

12. R2 Soft-Agar Overlays:

| Ingredient | Amount |
|---|---|
| Sucrose | 103.0 g |
| MgCl$_2$.6H$_2$O | 10.12 g |
| CaCl$_2$.2H$_2$O (3.68%) | 100.0 ml |
| 0.25 M TES buffer, pH = 7.2 | 100.0 ml |
| Agar | 4.1 g |

Deionized water is added to bring the final volume to one liter. The CaCl$_2$ and TES are filter sterilized and added after the other ingredients have been heat-sterilized (121° C. for 20 minutes).

B. Preparation and Storage of Protoplasts

The procedure described in this Example was used to construct and analyze *Streptomyces lividans* TK23 (NRRL 15826) transformants.

*Streptomyces lividans* TK23 was grown for 40–48 hours at 30° C. in YEME+34% sucrose, 5 mM MgCl$_2$, and 0.5% glycine. The mycelium was recovered by centrifugation (800Xg for 10 minutes in a bench top centrifuge) and washed twice in 10.3% sucrose. The mycelium from 25–50 ml of culture was suspended in 3–4 ml of L medium and incubated for 1 hour at 32° C. During this interval, the suspension was pipetted up and down once or twice to disperse clumps. Five ml of P medium were added to the suspension, which was then filtered through a plug of cotton wool. The protoplasts were recovered by centrifugation (800Xg for 10 minutes) and washed twice with 5 ml of P medium. The protoplasts were then suspended in 5 ml of P medium and the number of protoplasts determined microscopically using a hemacytometer slide. If the protoplasts are not to be used immediately, the suspension can be divided into aliquots (about 1 ml) containing $5 \times 10^9 - 10^{10}$ protoplasts in sterile polypropylene screw-cap tubes. The suspensions were frozen slowly by placing the tubes in a container of ice, which was in turn placed at −70° C. The protoplasts were stored at this temperature until needed. The frozen suspension was thawed rapidly by immersion in a 37° C. water bath prior to use.

C. Protoplast Transformation

Approximately $5 \times 10^9$ protoplasts were pelleted by centrifugation (800Xg for 10 minutes). The supernatant was decanted and the protoplasts were resuspended in the small volume of liquid remaining in the tube. Plasmid DNA in a volume not greater than 20 μl in TE buffer was added, followed immediately by the addition of 0.5 ml of T medium. The mixture was pipetted up and down once or twice to mix the contents. At this point the suspension was plated, either directly or after dilution with 0.5 ml of P medium. In either case, about 0.1 ml was inoculated per plate of R2YE medium.

Although the tlrC gene does not confer tylosin resistance to *Streptomyces lividans*, the tlrA and tlrB genes do confer tylosin resistance to *S. lividans*. Tylosin-resistant transformants were selected by replica-plating regenerated protoplasts to R2YE medium containing 500 µg/ml of tylosin. Alternatively, tylosin-resistant transformants can be selected by overlaying the regenerating protoplasts with soft nutrient broth agar containing tylosin. The regeneration plates are incubated for 16–22 hours at 30° C. before the application of 2.5 ml per plate of SNA (at a temperature of 45°–50° C.) containing enough tylosin to give a final concentration of 500 µg/ml after diffusion. If the transforming DNA only confers thiostrepton or hygromycin resistance, transformants are selected as described above, except that tylosin is replaced by thiostrepton (final concentration of 20 µg/ml) or hygromycin (final concentration of 200 µg/ml). Melanin production, or lack thereof, by transformants carrying pIJ702 derivatives was detected by incorporating tyrosine at 750 µg/ml into the SNA overlay; those transformants possessing an intact tyrosinase gene become black after growth in the presence of tyrosine.

D. Analysis of *Streptomyces lividans* TK23 Transformants

The transformants are cultured on R2YE agar supplemented with the appropriate antibiotic to obtain single colonies. These single colonies are used to inoculate 10 ml TSB cultures also containing antibiotic. The cultures are homogenized and then grown overnight at 30° C. in a rotary shaker.

Plasmid isolation for analysis is done by a small-scale version of the protocol of Example 1; the CsCl gradients of Example 1 are replaced by ethanol precipitations. The mycelium is collected by centrifugation, washed twice with 10.3% sucrose and then suspended in 1–2 ml of 10.3% sucrose. Four hundred µl of the cell mixture are transferred to a small tube, and 100 µl of 5X Lysozyme solution (Example 1) are added. The suspension is incubated at 30° C. for 30–60 minutes, followed by the addition and mixing of 300 µl of 0.3M NaOH containing 1% SDS. The latter solution is kept at 50° C. before its addition to the cell mix. The cell mixture is placed at 60° C. for 10 minutes, cooled to room temperature, and then extracted with 200 µl of phenol:CHCl₃ (50:50). The aqueous phase is transferred to a clean tube, made 0.3M in NaOAc, and then, one volume of isopropanol is added. The DNA is incubated at room temperature for five minutes and then pelleted by centrifugation. The pellet is dissolved in 400 µl of TE buffer and made 0.3M in NaOAc. About 2.5 volumes of ethanol are added, and the mixture is incubated at −70° C. for 30 minutes. After centrifugation and another precipitation, the plasmid DNA is suspended in 50 µl of TE buffer. Restriction enzyme cutting and electrophoretic analysis of the reaction products are used to determine plasmid structure.

EXAMPLE 9

Construction of Plasmids pSVB59, pSVB60, pSVB61, and pSVB62

A. Construction of Plasmid pSVB55

About 500 ng (5 µl) of plasmid pUC19 (ATCC 37254) are added to 2 µl of 10X SacI buffer, 12 µl of H₂O, and 1.5 µl (~15 units) of restriction enzyme SacI, an isoschizomer of restriction enzyme SstI. The resulting reaction is incubated at 37° C. for one hour, when about 3 µl of the reaction mixture are removed and subjected to agarose gel electrophoresis to determine completeness of digestion. About 4 µl of 10X KpnI buffer, 16 µl of H₂O, and 2 µl (~16 units) of restriction enzyme KpnI are added to the solution of SacI-digested plasmid pUC19 DNA, and the resulting reaction is incubated at 37° C. for 1 hour. About 6 µl of the reaction mixture are removed to check completeness of digestion. Then, the SacI-KpnI-digested DNA is collected by adjusting the NaOAc concentration of the reaction mixture to 0.30M, adding two volumes of ethanol, chilling the reaction mixture to −70° C., and centrifuging to pellet the precipitated DNA. The pellet of KpnI-SacI-digested plasmid pUC19 DNA is resuspended in 100 µl of 50 mM Tris-HCl, pH=8.0. About 1 µl of a 1:100 dilution of calf-intestinal alkaline phosphatase (Boehringer-Mannheim) in 50 mM Tris-HCl, pH=8, is added to the solution of DNA, and the resulting reaction is incubated at 37° C. for 30 minutes. The reaction is terminated by incubating the reaction mixture at 70° C. for one hour.

*Streptomyces lividans*/pSVB25 was cultured and plasmid pSVB25 isolated in substantial accordance with the teaching of Example 1. Thiostrepton selection (10 µg/ml) was used to ensure plasmid pSVB25 maintenance. The ~100 µg of plasmid pSVB25 DNA obtained were suspended in 1 ml of TE and stored at 4° C. About 625 ng of plasmid pSVB25 DNA in 25 µl of TE buffer are added to 6 µl of 10X SacI buffer, 26 µl of H₂O, and 2 µl (~20 units) each of restriction enzymes SacI and KpnI, and the resulting reaction is incubated at 37° C. for one hour. About 8 µl of the reaction mixture are subjected to agarose gel electrophoresis to check completeness of the digestions, and 3 µl of 1M NaCl and 2 µl of restriction enzyme ClaI are then added to the remainder of the reaction mixture, which is incubated at 37° C. for another hour. The ClaI-digestion lowers the frequency of undesired ligation products during the ligation to construct plasmid pSVB55. About 8 µl of the reaction mixture are removed to check the completeness of the ClaI digestion.

About 77 µl of the KpnI-SacI-digested, alkaline phosphatase-treated plasmid pUC19 DNA are added to 32 µl of the KpnI-SacI-ClaI-digested plasmid pSVB25 DNA, 11 µl of 3M NaOAc, and 300 µl of absolute ethanol. The solution is mixed, chilled at −70° C. for 30 minutes, and then centrifuged to pellet the DNA. The DNA is resuspended in 12 µl of 1X ligase buffer, and about 1 µl (~1 unit, Boehringer-Mannheim) of T4 DNA ligase is added to the solution of DNA. The resulting reaction is incubated at 15° C. overnight (~16 hours). The ligated DNA constitutes the desired plasmid pSVB55 DNA. A restriction site and function map of plasmid pSVB55 is presented in FIG. 16 of the accompanying drawings.

The ligated DNA is used to transform *E. coli* K12 JM109 in substantial accordance with the procedure of Example 3. Plasmid pUC19, like plasmid pHJL401, encodes the lacZ α-fragment, and the SacI and KpnI restriction enzyme recognition sites on plasmid pUC19 are located within the lacZ α-fragment-encoding DNA. Consequently, the transformed cells are plated on L agar containing ampicillin, X-Gal, and IPTG. The plasmid DNA of the colorless ("white"), ampicillin-resistant transformants is subjected to restriction enzyme analysis to identify the desired *E. coli* K12

JM109/pVB55 transformants. Plasmid pSVB55 DNA is prepared from the E. coli K12 JM109/pSVB55 transformants for use in the construction of plasmids pSVB56 and pSVB58 is substantial accordance with the procedure described in Example 3.

B. Construction of Plasmids pSVB56 and pSVB58

Plasmid pSVB2 DNA was prepared from Streptomyces lividans TK23/pSVB2 (NRRL 15880) in substantial accordance with the procedure of Example 1. The ~100 µg of plasmid pSVB2 DNA obtained were suspended in TE buffer at a concentration of 1 µg/µl. Approximately 50 µg (50 µl) of plasmid pSVB2 DNA are mixed with 10 µl of 10X KpnI buffer (60 mM NaCl; 60 mM Tris-HCl, pH=7.5; 60 mM MgCl$_2$; 60 mM 2-mercaptoethanol; and 1 mg/ml BSA), 5 µl (~50 units) of restriction enzyme KpnI and 35 µl H$_2$O and reacted at 37° C. for two hours. After heat inactivation, the reaction mixture is loaded into an agarose gel and the desired ~2.67 kb KpnI restriction fragment purified in substantial accordance with the procedure described in Example 3. The ~10 µg of the tlrA gene-containing, ~2.67 kb KpnI restriction fragment obtained are suspended in 100 µl of TE buffer and stored at 4° C.

Approximately 1 µg (1 µl) of the plasmid pSVB55 DNA isolated in Example 9A is mixed with 5 µl 10X KpnI buffer, 2 µl restriction enzyme KpnI (10 units), and 33 µl H$_2$O and reacted at 37° C. for two hours. The reaction is terminated by heat inactivation at 65° C. for 10 minutes.

Five µl of the ~2.6 kb KpnI restriction fragment of plasmid pSVB2 are mixed with 25 µl of the KpnI-digested plasmid pSVB55 and then precipitated by adding 3 µl of 3M NaOAc and 75 µl of ethanol, chilling at −70° C. for 30 minutes, and centrifuging. The resulting DNA pellet is suspended in 39 µl of 1X ligase buffer and 1 µl T4 DNA ligase and incubated overnight at 16° C. The ligated DNA constitutes the desired plasmids pSVB56 and pSVB58. The two plasmids differ only with respect to the orientation of the ~2.67 kb KpnI restriction fragment. A restriction site and function map of plasmid pSVB56 is presented in FIG. 17 of the accompanying drawings. The ligated DNA is used to transform E. coli K12 JM109 in substantial accordance with the procedure of Example 3, except that neither X-gal nor IPTG is added to the ampicillin-containing plates. The desired E. coli K12 JM109/pSVB56 and E. coli K12 JM109/pSVB58 transformants are identified by their ampicillin-resistant phenotype and by restriction enzyme analysis of their plasmid DNA. Plasmid pSVB56 and pSVB58 DNA is prepared from the transformants for use in the construction of plasmids pSVB59, pSVB60, pSVB61, and pSVB62 in substantial accordance with the plasmid isolation procedure described in Example 3.

C. Final Construction of Plasmids pSVB59, pSVB60, pSVB61, and pSVB62

About 5 µg of plasmid pSVB56 DNA in 5 µl of TE buffer are added to 2 µl of 10X HindIII buffer (0.5M NaCl; 0.5M Tris-HCl, pH=8; 0.1M MgCl$_2$; and 1 mg/ml BSA), 1 µl (~20 units) of restriction enzyme HindIII, and 12 µl of H$_2$O, and the resulting reaction is incubated at 37° C. for 2 hours. The HindIII-digested plasmid pSVB56 DNA is then precipitated with ethanol and NaOAc and resuspended in 17 µl of H$_2$O. About 2 µl of 10X EcoRI buffer (1M Tris-HCl, pH=7.5; 0.5M NaCl; 50 mM MgCl$_2$; and 1 mg/ml BSA) and 1 µl (~20 units) of restriction enzyme EcoRI are added to the solution of HindIII-digested plasmid pSVB56 DNA, and the resulting reaction is incubated at 37° C. for two hours. The EcoRI-HindIII-digested plasmid pSVB56 DNA is loaded onto an agarose gel and subjected to electrophoresis until the ~4.7 kb, tlrA-tlrB-containing restriction fragment is separated from the other digestion products. The ~4.7 kb fragment is isolated from the gel and purified in substantial accordance with the procedure of Example 3; about 1 µg of the fragment is obtained.

About 1 µg of plasmid pSVB49 is digested with restriction enzymes EcoRI and HindIII as described above. The digestions are terminated by incubating the reaction mixture at 70° C. About 0.1 µg of the EcoRI-HindIII-digested plasmid pSVB49 DNA is mixed with about 0.5 µg of the ~4.7 kb EcoRI-HindIII restriction fragment of plasmid pSVB56, and then, the DNA is precipitated with ethanol and NaOAc. The DNA is resuspended in 10 µl of 1X ligase buffer containing 6 units of T4 DNA ligase (Boehringer-Mannheim), and the resulting reaction is incubated at 4° C. overnight (~16 hours).

The ligated DNA constitutes the desired plasmid pSVB59 and is used to transform E. coli K12 JM109 in substantial accordance with the procedure of Example 3. The E. coli K12 JM109/pSVB59 transformants are selected on the basis of their ampicillin-resistant phenotype and identified by restriction enzyme analysis of their plasmid DNA. Plasmid pSVB59 DNA is prepared from the transformants in accordance with the procedure described in Example 3 and used to transform Streptomyces fradiae JS87 as described in Example 2. The S. fradiae JS87/pSVB59 transformants are identified by restriction enzyme analysis of their plasmid DNA and by their tylosin-resistant, thiostrepton-resistant phenotype. A restriction site and function map of plasmid pSVB59 is presented in FIG. 18 of the accompanying drawings.

Plasmid pSVB60 is constructed in substantial accordance with the protocol for constructing plasmid pSVB59, except that plasmid pSVB50, rather than plasmid pSVB49, is used in the procedure. Plasmid pSVB61 is constructed in substantial accordance with the protocol for constructing plasmid pSVB59, except that plasmid pSVB58, rather than plasmid pSVB56, is used in the procedure. Plasmid pSVB62 is constructed in substantial accordance with the protocol for constructing plasmid pSVB61, except that plasmid pSVB50, rather than plasmid pSVB49, is used in the procedure.

We claim:

1. The isolated tlrC gene of Streptomyces fradiae.
2. A recombinant DNA construct comprising the tlrC gene of Streptomyces fradiae.
3. The DNA of claim 2 that is the ~2.8 kb BamHI restriction fragment of plasmid pSKC10.
4. The recombinant DNA construct of claim 2 that is a recombinant DNA cloning vector.
5. A recombinant DNA cloning vector of claim 4 that is a plasmid.
6. A plasmid of claim 5 selected from the group consisting of plasmids pHDM101, pHDM102, pSKC10, pSKC11, pSKC12, pSKC30, pSKC31, pSKC32, pSKC33, pSKC34, pSKC35, pSKC36, pSKC37, pSKC38, pSKC39, pSKCAA, pSKCBB, pSKCEE, pSKCFF, pSVB48, pSVB49, pSVB50, pSVB51, pSVB52, pSVB53, pSVB54, pSVB57, pSVB59, pSVB60, pSVB61, and pSVB62.

7. The plasmid of claim 6 that is plasmid pSKC10.

8. The plasmid of claim 6 that is plasmid pSKC11.

9. The plasmid of claim 6 that is plasmid pSKCAA.

10. The plasmid of claim 6 that is plasmid pSVB49.

11. The plasmid of claim 6 that is plasmid pSKCEE.

12. The plasmid of claim 6 that is plasmid pSVB51.

13. The plasmid of claim 6 that is plasmid pSVB48.

14. A host cell transformed with a recombinant DNA cloning vector of claim 4.

15. A host cell transformed with a plasmid of claim 5.

16. The host cell of claim 15 that is Streptomyces.

17. The host cell of claim 16 that is selected from the group consisting of *Streptomyces fradiae* and *Streptomyces fradiae* JS87.

18. The host cell of claim 17 that is *S. fradiae* JS87/pSKC10.

19. The host cell of claim 17 that is *S. fradiae* JS87/pSKC11.

20. The host cell of claim 17 that is *S. fradiae* JS87/pSKCAA.

21. The host cell of claim 17 that is *S. fradiae* JS87/pSVB49.

22. The host cell of claim 17 that is *S. fradiae* JS87/pSKCEE.

23. The host cell of claim 17 that is *S. fradiae* JS87/pSVB51.

24. The host cell of claim 17 that is *S. fradiae* JS87/pSVB48.

25. A plasmid selected from the group consisting of plasmids pSVB34, pSVB55, pSVB56, and pSVB58.

* * * * *